US011800899B2

(12) United States Patent
Yamada et al.

(10) Patent No.: US 11,800,899 B2
(45) Date of Patent: Oct. 31, 2023

(54) AEROSOL GENERATING APPARATUS

(71) Applicant: JAPAN TOBACCO INC., Tokyo (JP)

(72) Inventors: Manabu Yamada, Tokyo (JP); Takeshi Akao, Tokyo (JP); Kazuma Mizuguchi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 582 days.

(21) Appl. No.: 16/850,007

(22) Filed: Apr. 16, 2020

(65) Prior Publication Data

US 2020/0237010 A1 Jul. 30, 2020

Related U.S. Application Data

(63) Continuation of application No. PCT/JP2017/038392, filed on Oct. 24, 2017.

(51) Int. Cl.

| | |
|---|---|
| ***A24F 40/53*** | (2020.01) |
| ***A24F 40/57*** | (2020.01) |
| ***A24F 40/51*** | (2020.01) |
| ***A24F 40/50*** | (2020.01) |
| ***A24F 40/10*** | (2020.01) |

(52) U.S. Cl.

CPC .............. *A24F 40/53* (2020.01); *A24F 40/50* (2020.01); *A24F 40/51* (2020.01); *A24F 40/57* (2020.01); *A24F 40/10* (2020.01)

(58) Field of Classification Search

CPC ........... A24F 40/53; A24F 40/51; A24F 40/57

See application file for complete search history.

(56) References Cited

U.S. PATENT DOCUMENTS 5,144,962 A 9/1992 Counts et al.
9,763,476 B2 9/2017 Flick
(Continued)

FOREIGN PATENT DOCUMENTS

JP 03-232481 A 10/1991
JP 2000-041654 A 2/2000
(Continued)

OTHER PUBLICATIONS

Blix Tutorial, Piezo Materials, downloaded online Nov. 4, 2022 (Year: 2022).*

(Continued)

*Primary Examiner* — Anthony Calandra
(74) *Attorney, Agent, or Firm* — XSENSUS LLP

(57) ABSTRACT

An aerosol generating apparatus comprises: a power source; a load configured to have an electric resistance value that varies according to a temperature and atomize an aerosol source or heat a flavor source when supplied with power from the power source; a feed circuit that is electrically connected to the power source and the load and includes a voltage conversion unit capable of converting an output voltage of the power source and outputting the converted output voltage to the load; and a control unit configured to acquire a measurement value corresponding to a current value of a current flowing through the load and control power supply to the load, wherein, in accordance with the measurement value, the control unit controls the feed circuit such that the measurement value becomes smaller than the target value or values included in the target range.

11 Claims, 11 Drawing Sheets

(56) References Cited

U.S. PATENT DOCUMENTS

| | | | |
|---|---|---|---|
| 10,470,495 | B2 | 11/2019 | Sur et al. |
| 10,575,561 | B2 | 3/2020 | Reevell |
| 10,582,726 | B2 | 3/2020 | Sur et al. |
| 10,701,971 | B2 | 7/2020 | Amir |
| 10,918,134 | B2 | 2/2021 | Sur et al. |
| 11,278,060 | B1 | 3/2022 | Aradachi |
| 2013/0319435 | A1 | 12/2013 | Flick |
| 2014/0253144 | A1 | 9/2014 | Novak, III et al. |
| 2014/0270727 | A1 | 9/2014 | Ampolini et al. |
| 2014/0299141 | A1 | 10/2014 | Flick |
| 2014/0338685 | A1 | 11/2014 | Amir |
| 2014/0345635 | A1 | 11/2014 | Rabinowitz et al. |
| 2016/0174611 | A1 | 6/2016 | Monsees et al. |
| 2016/0374398 | A1 | 12/2016 | Amir |
| 2017/0006917 | A1 | 1/2017 | Alvarez |
| 2017/0095005 | A1 | 4/2017 | Monsees et al. |
| 2017/0112191 | A1 | 4/2017 | Sur et al. |
| 2017/0112194 | A1 | 4/2017 | Sur et al. |
| 2017/0112195 | A1 | 4/2017 | Sur et al. |
| 2017/0112196 | A1 | 4/2017 | Sur et al. |
| 2017/0135405 | A1 | 5/2017 | Reevell |
| 2017/0138879 | A1 | 5/2017 | Akiyama |
| 2017/0231282 | A1 | 8/2017 | Bowen et al. |
| 2019/0014819 | A1* | 1/2019 | Sur ..................... B05B 17/0669 |
| 2019/0183186 | A1* | 6/2019 | Qiu ......................... A24F 40/50 |
| 2020/0138111 | A1 | 5/2020 | Angelico et al. |
| 2020/0154774 | A1 | 5/2020 | Reevell |
| 2020/0237006 | A1 | 7/2020 | Akao et al. |
| 2020/0337379 | A1 | 10/2020 | Amir |
| 2021/0089946 | A1 | 3/2021 | Pegors et al. |
| 2021/0127756 | A1 | 5/2021 | Sur et al. |
| 2021/0153562 | A1 | 5/2021 | Fishwick et al. |
| 2022/0015449 | A1 | 1/2022 | Gallagher et al. |
| 2022/0071303 | A1 | 3/2022 | Aradachi |

FOREIGN PATENT DOCUMENTS

| | | | |
|---|---|---|---|
| JP | 2005-525131 | A | 8/2005 |
| JP | 2005-255078 | A | 9/2005 |
| JP | 2011-515093 | A | 5/2011 |
| JP | 2013-509160 | A | 3/2013 |
| JP | 2014-501105 | A | 1/2014 |
| JP | 2014-501106 | A | 1/2014 |
| JP | 2014-501107 | A | 1/2014 |
| JP | 2014-512207 | A | 5/2014 |
| JP | 2015-507476 | A | 3/2015 |
| JP | 2015-531600 | A | 11/2015 |
| JP | 2017-501805 | A | 1/2017 |
| KR | 10-2016-0048033 | A | 5/2016 |
| WO | 96/39879 | A1 | 12/1996 |
| WO | 03/012565 | A1 | 2/2003 |
| WO | 2009/118085 | A1 | 10/2009 |
| WO | 2011/050964 | A1 | 5/2011 |
| WO | 2012/027350 | A2 | 3/2012 |
| WO | 2012/085203 | A1 | 6/2012 |
| WO | 2012/085205 | A1 | 6/2012 |
| WO | 2012/085207 | A1 | 6/2012 |
| WO | 2013/098396 | A1 | 7/2013 |
| WO | 2014/040988 | A2 | 3/2014 |
| WO | 2015/100361 | A1 | 7/2015 |
| WO | 2017/021550 | A1 | 2/2017 |
| WO | 2017/147560 | A1 | 8/2017 |

OTHER PUBLICATIONS

Analog Devices, ADP1614 Data sheet, 2014. (Year: 2014).*

Extended European search report dated Oct. 8, 2021, in corresponding European patent Application No. 17929756.9, 13 pages.

U.S. Office Action dated Mar. 25, 2022 in U.S. Appl. No. 16/850,012.

International Search Report and Written Opinion dated Jan. 23, 2018 for PCT/JP2017/038392 filed on Oct. 24, 2017, 11 pages including English Translation of the International Search Report.

Extended European search report dated Jun. 2, 2021, in corresponding European patent Application No. 17930120.5, 9 pages.

* cited by examiner

AEROSOL GENERATING APPARATUS

CROSS-REFERENCE TO RELATED APPLICATION(S)

This application is a continuation of International Patent Application No. PCT/JP2017/038392 filed on Oct. 24, 2017, the entire disclosures of which are incorporated herein by reference.

BACKGROUND OF THE INVENTION

Field of the Invention

The present invention relates to an aerosol generating apparatus.

Description of the Related Art

Aerosol generating apparatuses (electronic vaporization apparatuses), such as so-called electronic cigarettes and nebulizers (inhalers), that atomize (aerosolize) a liquid or a solid, which is an aerosol source, using a load that operates when supplied with power from a power source, such as a heater or an actuator, to allow a user to inhale the atomized liquid or solid are known.

For example, a system for generating inhalable vapor using an electronic vaporization apparatus is proposed (for example, PTL1). With this technology, whether or not vaporization is occurring is determined by monitoring power supplied to a coil that corresponds to a heater for atomizing an aerosol source. It is described that a reduction in power required to keep the coil at a set temperature indicates that there is not enough liquid in a fluid wick for normal vaporization to occur.

Also, an aerosol generating apparatus is proposed (for example, PTL2) that detects the presence of an aerosol forming substrate that includes or corresponds to an aerosol source in the proximity of a heating element configured to heat the aerosol forming substrate, by comparing, with a threshold value, power or energy that needs to be supplied to the heating element to keep the temperature of the heating element at a target temperature.

CITATION LIST

Patent Literature

PTL1: Japanese Patent Laid-Open No. 2017-501805
PTL2: Japanese Patent Laid-Open No. 2015-507476
PTL3: Japanese Patent Laid-Open No. 2005-525131
PTL4: Japanese Patent Laid-Open No. 2011-515093
PTL5: Japanese Patent Laid-Open No. 2013-509160
PTL6: Japanese Patent Laid-Open No. 2015-531600
PTL7: Japanese Patent Laid-Open No. 2014-501105
PTL8: Japanese Patent Laid-Open No. 2014-501106
PTL9: Japanese Patent Laid-Open No. 2014-501107
PTL10: International Publication No. 2017/021550
PTL11: Japanese Patent Laid-Open No. 2000-041654
PTL12: Japanese Patent Laid-Open No. 3-232481
PTL13: International Publication No. 2012/027350
PTL14: International Publication No. 1996/039879
PTL15: International Publication No. 2017/021550

When an aerosol is generated using an ordinary aerosol generating apparatus, power supply from a power source to a heater is controlled such that the temperature of the heater is near the boiling point of an aerosol source. If a sufficient quantity of the aerosol source is remaining and the aerosol generation quantity is controlled, power supplied from the power source to the heater has a constant value or shows a continuous change. In other words, if a sufficient quantity of the aerosol source is remaining and feedback control is performed to keep the heater temperature at a target temperature or in a target temperature range, power supplied from the power source to the heater has a constant value or shows a continuous change.

The remaining quantity of the aerosol source is an important variable that is used in various kinds of control performed by the aerosol generating apparatus. If the remaining quantity of the aerosol source is not detected or cannot be detected with sufficiently high precision, for example, there is a risk that power supply from the power source to the heater will be continued even if the aerosol source has been already depleted, and the charge amount of the power source will be wasted.

Therefore, the aerosol generating apparatus proposed in PTL2 determines whether there is a sufficient quantity of the aerosol source based on power required to maintain the temperature of the heater. However, power is generally measured using a plurality of sensors, and it is difficult to accurately estimate the remaining quantity of the aerosol source or depletion thereof based on the measured power unless errors of these sensors are accurately calibrated or control that takes errors into consideration is established.

As other methods for detecting the remaining quantity of the aerosol source, methods that use the temperature of the heater or the electric resistance value of the heater as described in PTL3 and PTL4 are proposed. It is known that the temperature and the electric resistance value of the heater take different values between a case in which a sufficient quantity of the aerosol source is remaining and a case in which the aerosol source is depleted. However, dedicated sensors or a plurality of sensors are necessary for these methods, and therefore it is also difficult to accurately estimate the remaining quantity of the aerosol source or depletion thereof using these methods.

Therefore, the present invention aims to provide an aerosol generating apparatus, a method for controlling an aerosol generating apparatus, a method for estimating a remaining quantity of an aerosol source or a flavor source, and a program for causing a processor to execute these methods, that improve precision of estimation of the remaining quantity of the aerosol source or depletion thereof.

SUMMARY OF THE INVENTION

An aerosol generating apparatus includes a power source, a load configured to have an electric resistance value that varies according to a temperature and atomize an aerosol source or heat a flavor source when supplied with power from the power source, a feed circuit that is electrically connected to the power source and the load and includes a voltage conversion unit capable of converting an output voltage of the power source and outputting the converted output voltage to the load, and a control unit configured to acquire a measurement value corresponding to a current value of a current flowing through the load and control power supply to the load based on the measurement value. If the measurement value belongs to a prescribed range that includes a target value or a target range, the control unit controls the feed circuit such that the measurement value approaches the target value or the target range, and if the measurement value does not belong to the prescribed range, the control unit controls the feed circuit such that the measurement value becomes smaller than the target value or values included in the target range.

If the output voltage output to the load is controlled as described above, it is possible to reduce errors that might be included in measurement values used for control when estimating the remaining quantity of the aerosol source or depletion thereof, and precision of control performed according to the remaining quantity of the aerosol source can be improved, for example. Furthermore, if the measurement value does not belong to the prescribed range, it is supposed that the remaining quantity of the aerosol source is smaller than a predetermined reference, and accordingly the feed circuit is controlled to reduce the measurement value, and thus wasting of the charge amount of the power source can be suppressed.

A configuration is also possible in which, if the measurement value does not belong to the prescribed range, the control unit controls the feed circuit such that a current does not flow through the load. The power source may also be a constant voltage power source. A configuration is also possible in which, if the measurement value does not belong to the prescribed range, the control unit detects depletion of the aerosol source. A configuration is also possible in which, if the measurement value belongs to the prescribed range including the target value or the target range, the feed circuit is controlled in a first control mode such that the measurement value approaches the target value or the target range. At this time, a configuration is also possible in which, if the measurement value does not belong to the prescribed range, the feed circuit is controlled in a second control mode in which a change amount of the measurement value is larger than that in the first control mode. A configuration is also possible in which, if the measurement value does not belong to the prescribed range, the feed circuit is controlled such that the measurement value does not approach the target value or the target range.

A configuration is also possible in which the control unit acquires the measurement value while performing control such that the voltage conversion unit outputs a constant voltage. Specifically, if the voltage conversion unit is caused to output a constant voltage, for example, not only the resistance value, but also the temperature of the load can be determined by detecting a current value of a current flowing through the load. Thus, errors that might be included in variables used for control can be significantly reduced, when compared to a case in which measurement values detected by a plurality of sensors are used.

A configuration is also possible in which the feed circuit includes a first power supply path that does not output the measurement value and a second power supply path that outputs the measurement value. In this case, the second power supply path needs to be caused to function only when the remaining quantity of the aerosol source is to be estimated, and therefore wasting of the charge amount of the power source, which occurs if the remaining quantity is continuously estimated, can be avoided.

A configuration is also possible in which the feed circuit includes a sensor that is arranged at a position in series to the load and capable of outputting, as the measurement value, a current value of a current passing therethrough or a voltage value of a voltage applied thereto, and the control unit acquires the measurement value from the sensor. Specifically, the measurement value can be acquired using such a sensor.

A configuration is also possible in which the feed circuit includes a first power supply path that connects the power source to the load not via the sensor and a second power supply path that connects the power source to the load via the sensor, and the control unit performs control such that the first power supply path and the second power supply path do not function at the same time, and acquires the measurement value from the sensor included in the second power supply path. Thus, the above-described sensor can be provided on one of the power supply paths in a specific configuration.

A configuration is also possible in which the feed circuit includes a first node that is connected to the power source and from which the feed circuit branches into the first power supply path and the second power supply path and a second node that is connected to the load and at which the first power supply path and the second power supply path merge with each other. In other words, the circuit can be realized with a configuration branched as described above.

A configuration is also possible in which a current that flows through the second power supply path is smaller than a current that flows through the first power supply path. A configuration is also possible in which the voltage conversion unit converts the output voltage of the power source such that a current that flows through the second power supply path is smaller than a current that flows through the first power supply path. A configuration is also possible in which the control unit controls the first power supply path and the second power supply path such that a period for which power is supplied to the second power supply path is shorter than a period for which power is supplied to the first power supply path. A configuration is also possible in which the control unit controls the first power supply path and the second power supply path such that the frequency of power supply to the second power supply path is lower than the frequency of power supply to the first power supply path. Since a current that flows through the second power supply path, which is provided mainly for acquiring the measurement value, is only required to be large enough to output the measurement value, wasting of the charge amount of the power source can be consequently suppressed when acquiring the measurement value.

A configuration is also possible in which the control unit controls the second power supply path such that an amount of an aerosol generated by the load while the second power supply path is caused to function is smaller than an amount of the aerosol generated by the load while the first power supply path is caused to function. A configuration is also possible in which the aerosol generating apparatus further includes a mouthpiece end that is provided at an end portion of the aerosol generating apparatus to emit an aerosol into the mouth of a user, and the control unit controls the second power supply path such that the aerosol is not emitted from the mouthpiece end while the second power supply path is caused to function. When the second power supply path is caused to function, it is only required to be able to acquire the measurement value, and control may be performed to reduce the amount of the aerosol to be generated. A configuration is also possible in which the control unit controls the second power supply path such that the load does not generate an aerosol while the second power supply path is caused to function. In this case, when the second power supply path provided mainly for acquiring the measurement value is caused to function, not only wasting of the charge amount of the power source, but also wasting of the remaining quantity of the aerosol source can be suppressed. Also, generation of the aerosol can be suppressed in a situation in which the user of the aerosol generating apparatus does not intend to generate the aerosol.

A configuration is also possible in which the voltage conversion unit includes a linear regulator, and the linear regulator is provided between the first node and the sensor on the second power supply path. With this configuration, the occurrence of conversion loss (transition loss), conduction loss, switching loss, etc. at the linear regulator can be eliminated from the first power supply path.

A configuration is also possible in which the voltage conversion unit includes a switching regulator, and the switching regulator is provided between the power source and the first node in the feed circuit. With this configuration, controllability of the entire circuit can be improved while reducing loss.

A configuration is also possible in which the control unit controls the switching regulator such that power loss that occurs at the switching regulator when the first power supply path is caused to function is smaller than power loss that occurs at the switching regulator when the second power supply path is caused to function. A configuration is also possible in which the control unit performs control such that the switching regulator is in a direct coupling state when the first power supply path is caused to function. With this configuration, the power source can be more efficiently used to generate an aerosol in the first power supply path.

An aerosol generating apparatus according to another aspect of the present invention includes a power source, a load configured to have an electric resistance value that varies according to a temperature and atomize an aerosol source or heat a flavor source when supplied with power from the power source, a feed circuit that is electrically connected to the power source and the load and includes a voltage conversion unit capable of converting an output voltage of the power source and outputting the converted output voltage to the load, and a control unit configured to acquire a measurement value corresponding to a current value of a current flowing through the load and estimate a remaining quantity of the aerosol source or the flavor source based on the measurement value.

If the output voltage output to the load is controlled as described above, it is possible to reduce errors that might be included in variables used for control when estimating the remaining quantity of the aerosol source or depletion thereof, and precision of estimation of the remaining quantity of the aerosol source or the flavor source based on the measurement value can be improved.

Note that what are described in the solution to problem can be combined within a scope not departing from the problem to be solved by the present invention and the technical idea of the present invention. Also, what are described in the solution to problem can be provided as a system that includes one or more apparatuses that include a computer, a processor, an electric circuit, etc., a method to be executed by an apparatus, or a program to be executed by an apparatus. The program can also be executed on a network. A storage medium that holds the program may also be provided.

According to the present invention, it is possible to provide an aerosol generating apparatus, a method for controlling an aerosol generating apparatus, a method for estimating a remaining quantity of an aerosol source or a flavor source, and a program for causing a processor to execute these methods, that improve precision of estimation of the remaining quantity of the aerosol source or depletion thereof.

Further features of the present invention will become apparent from the following description of exemplary embodiments (with reference to the attached drawings).

DESCRIPTION OF THE EMBODIMENTS

An embodiment of an aerosol generating apparatus according to the present invention will be described based on the drawings. Dimensions, materials, shapes, relative arrangements, etc. of constitutional elements described in the present embodiment are examples. Also, the order of processes is one example, and the order can be changed or processes can be executed in parallel within a scope not departing from the problem to be solved by the present invention and the technical idea of the present invention. Therefore, the technical scope of the present invention is not limited to the following examples unless otherwise specified.

<Embodiment>

Figure 1:
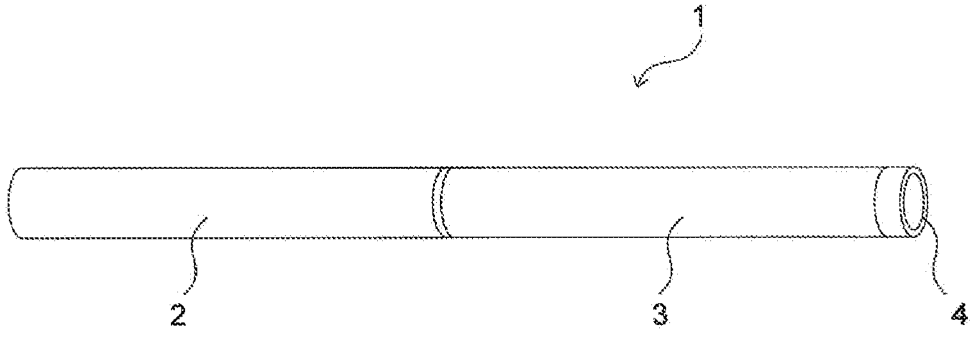
FIG. 1 is a perspective view showing one example of the external appearance of an aerosol generating apparatus.
Figure 2:
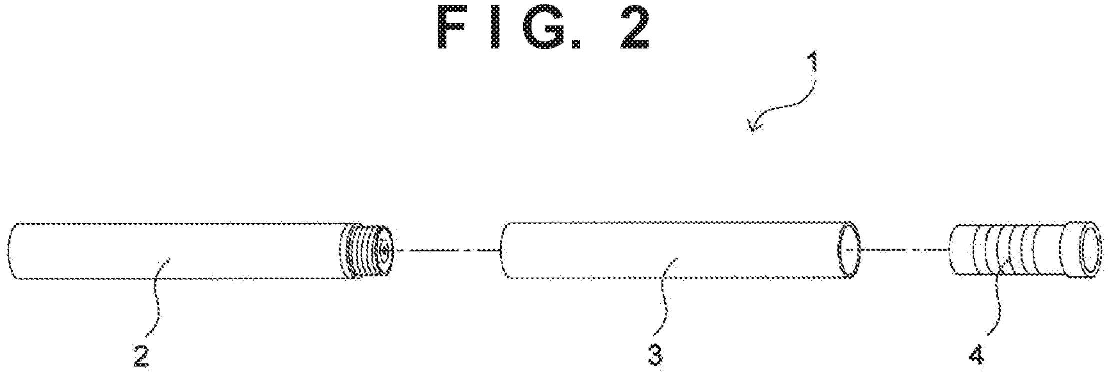
FIG. 2 is an exploded view showing one example of the aerosol generating apparatus.

FIG. 1 is a perspective view showing one example of the external appearance of an aerosol generating apparatus. FIG. 2 is an exploded view showing one example of the aerosol generating apparatus. An aerosol generating apparatus 1 is an electronic cigarette, a nebulizer, etc. and generates an aerosol in response to inhalation performed by a user and provides the aerosol to the user. Note that a single continuous inhaling action performed by a user will be referred to as a "puff". Also, in the present embodiment, the aerosol generating apparatus 1 adds a flavor component etc. to the generated aerosol and emits the aerosol into the mouth of the user.

As shown in FIGS. 1 and 2, the aerosol generating apparatus 1 includes a main body 2, an aerosol source holding portion 3, and an additive component holding portion 4. The main body 2 supplies power and controls operations of the entire apparatus. The aerosol source holding portion 3 holds an aerosol source to be atomized to generate an aerosol. The additive component holding portion 4 holds components such as a flavor component, nicotine, etc. A user can inhale the aerosol with added flavor etc. while holding a mouthpiece, which is an end portion on the additive component holding portion 4 side, in their mouth.

The aerosol generating apparatus 1 is formed as a result of the main body 2, the aerosol source holding portion 3, and the additive component holding portion 4 being assembled by the user, for example. In the present embodiment, the main body 2, the aerosol source holding portion 3, and the additive component holding portion 4 have a cylindrical shape, a truncated cone shape, etc. with a predetermined diameter, and can be coupled together in the order of the main body 2, the aerosol source holding portion 3, and the additive component holding portion 4. The main body 2 and the aerosol source holding portion 3 are coupled to each other by screwing together a male screw portion and a female screw portion that are respectively provided in end portions of the main body 2 and the aerosol source holding portion 3, for example. The aerosol source holding portion 3 and the additive component holding portion 4 are coupled to each other by fitting the additive component holding portion 4, which includes a side surface having tapers, into a tubular portion provided at one end of the aerosol source holding portion 3, for example. The aerosol source holding portion 3 and the additive component holding portion 4 may be disposable replacement parts.

<Internal Configuration>

Figure 3:
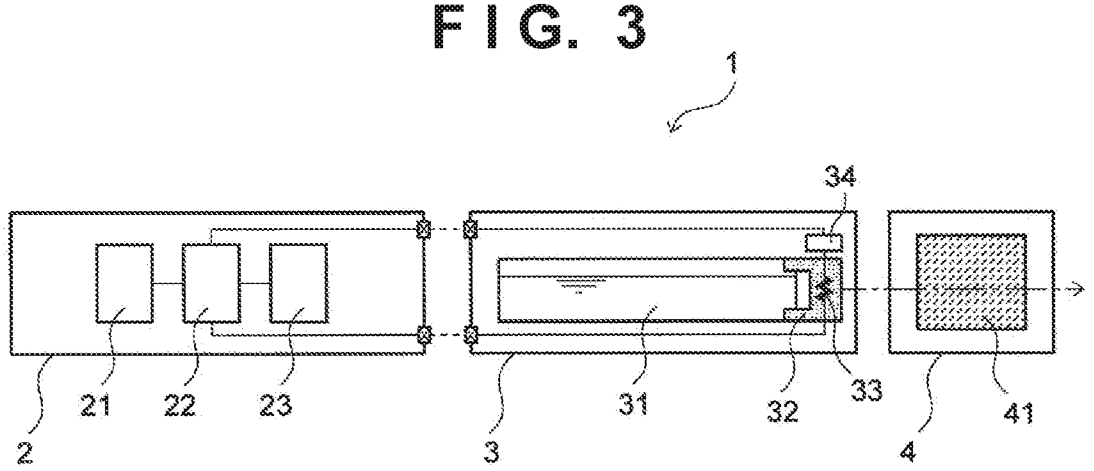
FIG. 3 is a schematic diagram showing one example of an internal structure of the aerosol generating apparatus.

FIG. 3 is a schematic diagram showing one example of the inside of the aerosol generating apparatus 1. The main body 2 includes a power source 21, a control unit 22, and an inhalation sensor 23. The control unit 22 is electrically connected to the power source 21 and the inhalation sensor 23. The power source 21 is a secondary battery, for example, and supplies power to an electric circuit included in the aerosol generating apparatus 1. The control unit 22 is a processor, such as a microcontroller (MCU: Micro-Control Unit), and controls operations of the electric circuit included in the aerosol generating apparatus 1. The inhalation sensor 23 is an air pressure sensor, a flow rate sensor, etc. When a user inhales from the mouthpiece of the aerosol generating apparatus 1, the inhalation sensor 23 outputs a value according to a negative pressure or the flow rate of a gas flow generated inside the aerosol generating apparatus 1. Namely, the control unit 22 can detect inhalation based on the output value of the inhalation sensor 23.

The aerosol source holding portion 3 of the aerosol generating apparatus 1 includes a storage portion 31, a supply portion 32, a load 33, and a remaining quantity sensor 34. The storage portion 31 is a container for storing a liquid aerosol source to be atomized through heating. Note that the aerosol source is a polyol-based material, such as glycerin or propylene glycol, for example. The aerosol source may also be a liquid mixture (also referred to as a "flavor source") that further contains a nicotine liquid, water, a flavoring agent, etc. Assume that such an aerosol source is stored in the storage portion 31 in advance. Note that the aerosol source may also be a solid for which the storage portion 31 is unnecessary.

The supply portion 32 includes a wick that is formed by twisting a fiber material, such as fiberglass, for example. The supply portion 32 is connected to the storage portion 31. The supply portion 32 is also connected to the load 33 or at least a portion of the supply portion 32 is arranged in the vicinity of the load 33. The aerosol source permeates through the wick by capillary action, and moves to a portion at which the aerosol source can be atomized as a result of being heated by the load 33. In other words, the supply portion 32 soaks up the aerosol source from the storage portion 31 and carries the aerosol source to the load 33 or the vicinity of the load 33. Note that porous ceramic may also be used for the wick, instead of fiberglass.

The load 33 is a coil-shaped heater, for example, and generates heat as a result of a current flowing through the load 33. For example, the load 33 has Positive Temperature Coefficient (PTC) characteristics, and the resistance value of the load 33 is substantially in direct proportion to the generated heat temperature. Note that the load 33 does not necessarily have to have Positive Temperature Coefficient characteristics, and it is only required that there is a correlation between the resistance value of the load 33 and the generated heat temperature. For example, a configuration is also possible in which the load 33 has Negative Temperature Coefficient (NTC) characteristics. Note that the load 33 may be wrapped around the wick or conversely, the circumference of the load 33 may be covered by the wick. The control unit 22 controls power supply to the load 33. When the aerosol source is supplied from the storage portion 31 to the load 33 by the supply portion 32, the aerosol source evaporates under heat generated by the load 33, and an aerosol is generated. If an inhaling action of the user is detected based on the output value of the inhalation sensor 23, the control unit 22 supplies power to the load 33 to generate the aerosol. If the remaining quantity of the aerosol source stored in the storage portion 31 is sufficiently large, a sufficient quantity of the aerosol source is supplied to the load 33 and heat generated by the load 33 is transferred to the aerosol source, in other words, heat generated by the load 33 is used for heating and vaporizing the aerosol source, and therefore the temperature of the load 33 almost never becomes higher than a predetermined temperature set in advance. On the other hand, if the aerosol source stored in the storage portion 31 is depleted, the quantity of the aerosol source supplied to the load 33 per unit time decreases. As a result, heat generated by the load 33 is not transferred to the aerosol source, in other words, heat generated by the load 33 is not used for heating and vaporizing the aerosol source, and therefore the load 33 is excessively heated and the resistance value of the load 33 is accordingly increased.

The remaining quantity sensor 34 outputs sensing data for estimating the remaining quantity of the aerosol source stored in the storage portion 31 based on the temperature of the load 33. The remaining quantity sensor 34 includes, for example, a resistor (shunt resistor) that is connected in series to the load 33 to measure a current, and a measurement apparatus that is connected in parallel to the resistor to measure the voltage value of the resistor. Note that the resistance value of the resistor is a constant value that is determined in advance and does not substantially vary according to the temperature. Therefore, the current value of a current flowing through the resistor can be determined based on the known resistance value and a measured voltage value.

Note that a measurement apparatus in which a hall element is used may also be used instead of the above-described measurement apparatus in which the shunt resistor is used. The hall element is arranged at a position in series to the load 33. Namely, a gap core that includes the hall element is arranged around a conducting wire that is connected in series to the load 33. The hall element detects a magnetic field generated by a current passing therethrough. In a case in which the hall element is used, the "current passing therethrough" means a current that flows through the conducting wire that is arranged at the center of the gap core and is not in contact with the hall element, and the current value of the current is the same as that of a current flowing through the load 33. In the present embodiment, the remaining quantity sensor 34 outputs the current value of a current flowing through the resistor. Alternatively, the voltage value of a voltage applied between opposite ends of the resistor may also be used, or a value obtained by performing a predetermined operation on the current value or the voltage value may also be used, rather than the current value or the voltage value itself. These measurement values that can be used instead of the current value of a current flowing through the resistor are values that vary according to the current value of a current flowing through the resistor. Namely, the remaining quantity sensor 34 is only required to output a measurement value corresponding to the current value of a current flowing through the resistor. It goes without saying that the technical idea of the present invention encompasses cases in which these measurement values are used instead of the current value of a current flowing through the resistor.

The additive component holding portion 4 of the aerosol generating apparatus 1 holds chopped tobacco leaves and a flavor component 41, such as menthol, therein. The additive component holding portion 4 includes air vents on the mouthpiece side and in a portion to be coupled to the aerosol source holding portion 3, and when the user inhales from the mouthpiece, a negative pressure is generated inside the additive component holding portion 4, the aerosol generated in the aerosol source holding portion 3 is sucked, nicotine, a flavor component, etc. are added to the aerosol in the additive component holding portion 4, and the aerosol is emitted into the mouth of the user.

Note that the internal configuration shown in FIG. 3 is one example. A configuration is also possible in which the aerosol source holding portion 3 is provided along a side surface of a cylinder and have a torus shape that includes a cavity extending along a center of a circular cross section. In this case, the supply portion 32 and the load 33 may be arranged in the central cavity. Furthermore, an output portion, such as an LED (Light Emitting Diode) or a vibrator, may be further provided to output the state of the apparatus to the user.

<Circuit Configuration>

Figure 4:
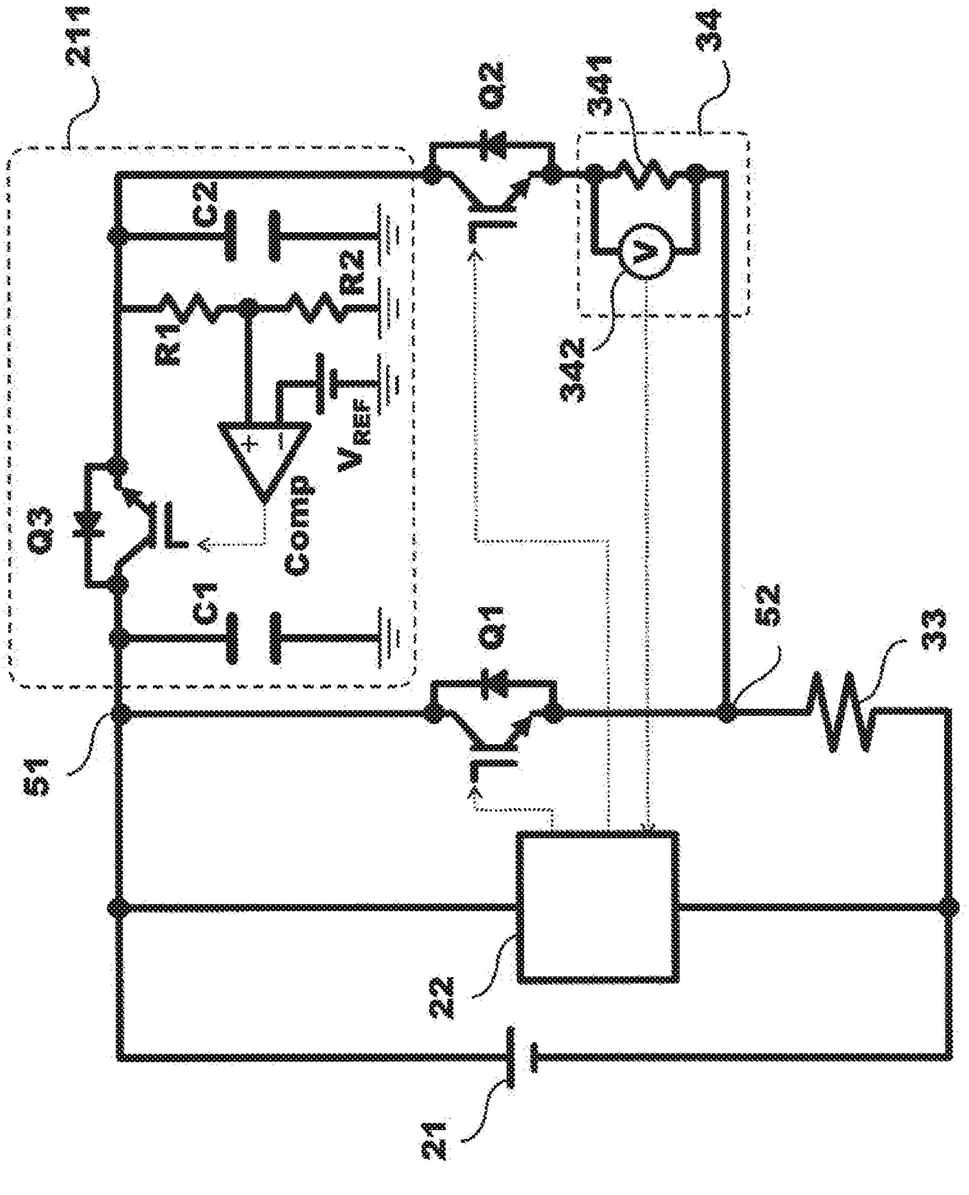
FIG. 4 is a circuit diagram showing one example of a circuit configuration of the aerosol generating apparatus.

FIG. 4 is a circuit diagram showing one example of a portion of a circuit configuration in the aerosol generating apparatus relating to detection of the remaining quantity of the aerosol source and control of power supply to the load. The aerosol generating apparatus 1 includes the power source 21, the control unit 22, a voltage conversion unit 211, switches (switching elements) Q1 and Q2, the load 33, and the remaining quantity sensor 34. A portion that connects the power source 21 to the load 33 and includes the switches Q1 and Q2 and the voltage conversion unit 211 will also be referred to as a "feed circuit" according to the present invention. The power source 21 and the control unit 22 are provided in the main body 2 shown in FIGS. 1 to 3, and the voltage conversion unit 211, the switches Q1 and Q2, the load 33, and the remaining quantity sensor 34 are provided in the aerosol source holding portion 3 shown in FIGS. 1 to 3, for example. As a result of the main body 2 and the aerosol source holding portion 3 being coupled together, constitutional elements therein are electrically connected to each other and a circuit as shown in FIG. 4 is formed. Note that a configuration is also possible in which at least some of the voltage conversion unit 211, the switches Q1 and Q2, and the remaining quantity sensor 34 are provided in the main body 2, for example. In a case in which the aerosol source holding portion 3 and the additive component holding portion 4 are configured as disposable replacement parts, the cost of the replacement parts can be reduced by reducing the number of components included in the replacement parts.

The power source 21 is directly or indirectly electrically connected to each constitutional element and supplies power to the circuit. The control unit 22 is connected to the switches Q1 and Q2 and the remaining quantity sensor 34. The control unit 22 acquires an output value of the remaining quantity sensor 34 to calculate an estimated value regarding the aerosol source remaining in the storage portion 31, and controls opening and closing of the switches Q1 and Q2 based on the calculated estimated value, an output value of the inhalation sensor 23, etc.

The switches Q1 and Q2 are semiconductor switches such as MOSFETs (Metal-Oxide-Semiconductor Field-Effect Transistors), for example. One end of the switch Q1 is connected to the power source 21 and another end of the switch Q1 is connected to the load 33. By closing the switch Q1, power can be supplied to the load 33 to generate an aerosol. The control unit 22 closes the switch Q1 upon detecting an inhaling action of the user, for example. Note that a path that passes the switch Q1 and the load 33 will also be referred to as an "aerosol generation path" and a "first power supply path".

One end of the switch Q2 is connected to the power source 21 via the voltage conversion unit 211 and another end of the switch Q2 is connected to the load 33 via the remaining quantity sensor 34. By closing the switch Q2, an output value of the remaining quantity sensor 34 can be acquired. Note that a path that passes the switch Q2, the remaining quantity sensor 34, and the load 33 and through which the remaining quantity sensor 34 outputs a prescribed measurement value will also be referred to as a "remaining quantity detection path" and a "second power supply path" according to the present invention. Note that, if a hall element is used in the remaining quantity sensor 34, the remaining quantity sensor 34 need not be connected to the switch Q2 and the load 33 and is only required to be provided to be able to output a prescribed measurement value at a position between the switch Q2 and the load 33. In other words, it is only required that a conducting wire that connects the switch Q2 to the load 33 passes through the hall element.

The above-described circuit shown in FIG. 4 includes a first node 51 from which a path extending from the power source 21 branches into the aerosol generation path and the remaining quantity detection path and a second node 52 that is connected to the load 33 and at which the aerosol generation path and the remaining quantity detection path merge with each other.

The voltage conversion unit 211 is capable of converting a voltage output by the power source 21 and outputting the converted voltage to the load 33. Specifically, the voltage conversion unit 211 is a voltage regulator, such as an LDO (Low Drop-Out) regulator shown in FIG. 4, and outputs a constant voltage. One end of the voltage conversion unit 211 is connected to the power source 21 and another end of the voltage conversion unit 211 is connected to the switch Q2. The voltage conversion unit 211 includes a switch Q3, resistors R1 and R2, capacitors C1 and C2, a comparator Comp, and a constant voltage source that outputs a reference voltage $V_{REF}$. Note that, if the LDO regulator shown in FIG. 4 is used, an output voltage $V_{out}$ of the LDO regulator can be determined using the following expression (1).

$$V_{out}=R_2/(R_1+R_2)\times V_{REF} \quad (1)$$

The switch Q3 is a semiconductor switch, for example, and is opened or closed according to output of the comparator Comp. One end of the switch Q3 is connected to the power source 21, and the output voltage is changed according to the duty ratio of opening and closing of the switch Q3. The output voltage of the switch Q3 is divided by the resistors R1 and R2 that are connected in series, and is applied to one input terminal of the comparator Comp. The reference voltage $V_{REF}$ is applied to another input terminal of the comparator Comp. Then, a signal that indicates the result of comparison between the reference voltage $V_{REF}$ and the output voltage of the switch Q3 is output. Even if the voltage value of a voltage applied to the switch Q3 varies, so long as the voltage value is at least a predetermined value, the output voltage of the switch Q3 can be made constant based on feedback received from the comparator Comp, as described above. The comparator Comp and the switch Q3 will also be referred to as a "voltage conversion unit" according to the present invention.

Note that one end of the capacitor C1 is connected to an end portion of the voltage conversion unit 211 on the power source 21 side and another end of the capacitor C1 is connected to the ground. The capacitor C1 stores power and protects the circuit from a surge voltage. One end of the capacitor C2 is connected to an output terminal of the switch Q3 and the capacitor C2 smoothes the output voltage.

If a power source such as a secondary battery is used, the power source voltage decreases as the charge rate decreases. With the voltage conversion unit 211 according to the present embodiment, a constant voltage can be supplied even if the power source voltage varies to some extent.

The remaining quantity sensor 34 includes a shunt resistor 341 and a voltmeter 342. One end of the shunt resistor 341 is connected to the voltage conversion unit 211 via the switch Q2. Another end of the shunt resistor 341 is connected to the load 33. Namely, the shunt resistor 341 is connected in series to the load 33. The voltmeter 342 is connected in parallel to the shunt resistor 341 and is capable of measuring a voltage drop amount at the shunt resistor 341. The voltmeter 342 is also connected to the control unit 22 and outputs the measured voltage drop amount at the shunt resistor 341 to the control unit 22.

<Remaining Quantity Estimation Processing>

Figure 5:
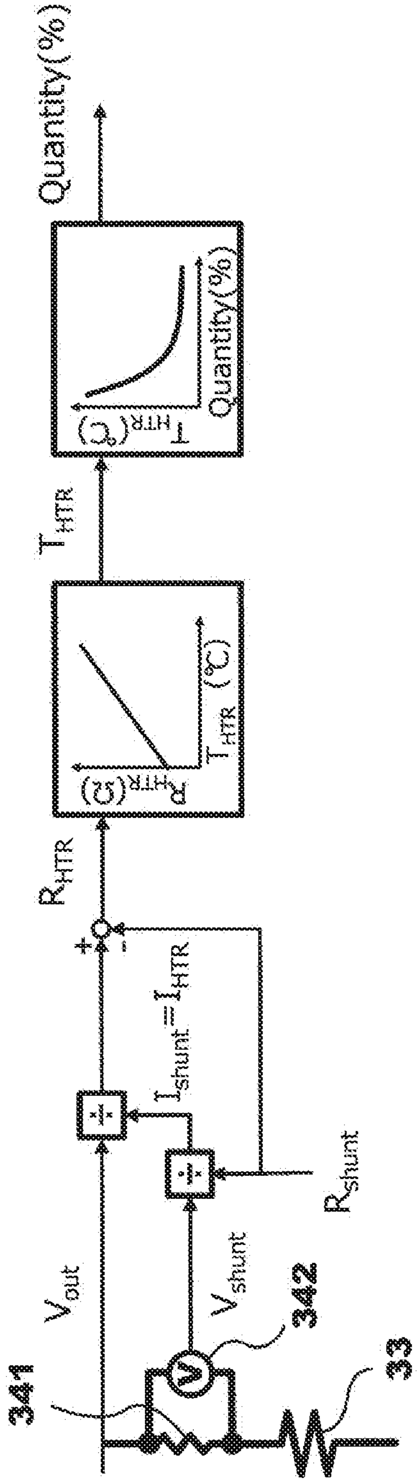
FIG. 5 is a block diagram showing processing for estimating the quantity of an aerosol source stored in a storage portion.

FIG. 5 is a block diagram showing processing for estimating the quantity of the aerosol source stored in the storage portion 31. Assume that a voltage $V_{out}$ that is output by the voltage conversion unit 211 is a constant. Also, a resistance value $R_{shunt}$ of the shunt resistor 341 is a known constant. Therefore, a current value $I_{shunt}$ of a current flowing through the shunt resistor 341 can be determined from a voltage $V_{shunt}$ between opposite ends of the shunt resistor 341 using the following expression (2).

$$I_{shunt}=V_{shunt}/R_{shunt} \quad (2)$$

Note that a current value $I_{HTR}$ of a current flowing through the load 33 connected in series to the shunt resistor 341 is equal to $I_{shunt}$. The shunt resistor 341 is connected in series to the load 33, and a value corresponding to the current value of a current flowing through the load is measured at the shunt resistor 341.

Here, the output voltage $V_{out}$ of the voltage conversion unit 211 can be expressed by the following expression (3) using a resistance value $R_{HTR}$ of the load 33.

$$V_{out}=I_{shunt}\times(R_{shunt}+R_{HTR}) \quad (3)$$

By transforming the expression (3), the resistance value $R_{HTR}$ of the load 33 can be expressed by the following expression (4).

$$R_{HTR}=V_{out}/I_{shunt}-R_{shunt} \quad (4)$$

The load 33 has the above-described Positive Temperature Coefficient (PTC) characteristics, and the resistance value $R_{HTR}$ of the load 33 is substantially in direct proportion to a temperature $T_{HTR}$ of the load 33 as shown in FIG. 5. Therefore, the temperature $T_{HTR}$ of the load 33 can be calculated based on the resistance value $R_{HTR}$ of the load 33. In the present embodiment, information that indicates a relationship between the resistance value $R_{HTR}$ and the temperature $T_{HTR}$ of the load 33 is stored in a table in advance, for example. Therefore, the temperature $T_{HTR}$ of the load 33 can be estimated without using a dedicated temperature sensor. Note that, in a case in which the load 33 has Negative Temperature Coefficient (NTC) characteristics as well, the temperature $T_{HTR}$ of the load 33 can be estimated based on information indicating a relationship between the resistance value $R_{HTR}$ and the temperature $T_{HTR}$.

In the present embodiment, even if the aerosol source around the load 33 is evaporated by the load 33, the aerosol source is continuously supplied via the supply portion 32 to the load 33 so long as a sufficient quantity of the aerosol source is stored in the storage portion 31. Therefore, if the quantity of the aerosol source remaining in the storage portion 31 is at least a predetermined quantity, normally, the temperature of the load 33 is not significantly increased exceeding the boiling point of the aerosol source. However, as the quantity of the aerosol source remaining in the storage portion 31 decreases, the quantity of the aerosol source supplied via the supply portion 32 to the load 33 also decreases, and the temperature of the load 33 is increased exceeding the boiling point of the aerosol source. Assume that information that indicates such a relationship between the remaining quantity of the aerosol source and the temperature of the load 33 is known in advance through experiments etc. Based on this information and the calculated temperature $T_{HTR}$ of the load 33, a remaining quantity of the aerosol source held by the storage portion 31 can be estimated. Note that the remaining quantity may also be determined as the ratio of the remaining quantity to the capacity of the storage portion 31.

Since there is a correlation between the remaining quantity of the aerosol source and the temperature of the load 33, it is possible to determine that the aerosol source in the storage portion 31 is depleted if the temperature of the load 33 exceeds a threshold value of the temperature that corresponds to a threshold value of the remaining quantity determined in advance. Furthermore, since there is correspondence between the resistance value and the temperature of the load 33, it is possible to determine that the aerosol source in the storage portion 31 is depleted if the resistance value of the load 33 exceeds a threshold value of the resistance value that corresponds to the above-described threshold value of the temperature. Also, the current value $I_{shunt}$ of a current flowing through the shunt resistor 341 is the only variable in the above-described expression (4), and accordingly a threshold value of the current value that corresponds to the above-described threshold value of the resistance value is uniquely determined. Here, the current value $I_{shunt}$ of a current flowing through the shunt resistor 341 is equal to the current value $I_{HTR}$ of a current flowing through the load 33. Therefore, it is also possible to determine that the aerosol source in the storage portion 31 is depleted if the current value $I_{HTR}$ of a current flowing through the load 33 is smaller than a threshold value of the current value determined in advance. Namely, with respect to a measurement value, such as the current value of a current caused to flow through the load 33, it is possible to determine a target value or a target range in a state in which a sufficient quantity of the aerosol source is remaining, for example, and determine whether the remaining quantity of the aerosol source is sufficiently large depending on whether or not the measurement value belongs to a prescribed range that includes the target value or the target range. The prescribed range can be determined using the above-described threshold value, for example.

As described above, according to the present embodiment, the resistance value $R_{shunt}$ of the load 33 can be calculated using one measurement value, i.e., the value $I_{shunt}$ of a current flowing through the shunt resistor 341. Note that the current value $I_{shunt}$ of a current flowing through the shunt resistor 341 can be determined by measuring the voltage $V_{shunt}$ between opposite ends of the shunt resistor 341 as shown by the expression (2). Here, a measurement value output by a sensor generally includes various errors, such as an offset error, a gain error, a hysteresis error, and a linearity error. In the present embodiment, the voltage conversion unit 211 that outputs a constant voltage is used, and accordingly, when estimating the remaining quantity of the aerosol source held by the storage portion 31 or determining whether or not the aerosol source in the storage portion 31 is depleted, the number of variables for which measurement values are to be substituted is one. Therefore, precision of the calculated resistance value $R_{HTR}$ of the load 33 is improved, when compared to a case in which the resistance value of the load etc. is calculated by substituting output values of different sensors for a plurality of variables, for example. As a result, precision of the remaining quantity of the aerosol source, which is estimated based on the resistance value $R_{HTR}$ of the load 33, is also improved.

Figure 6:
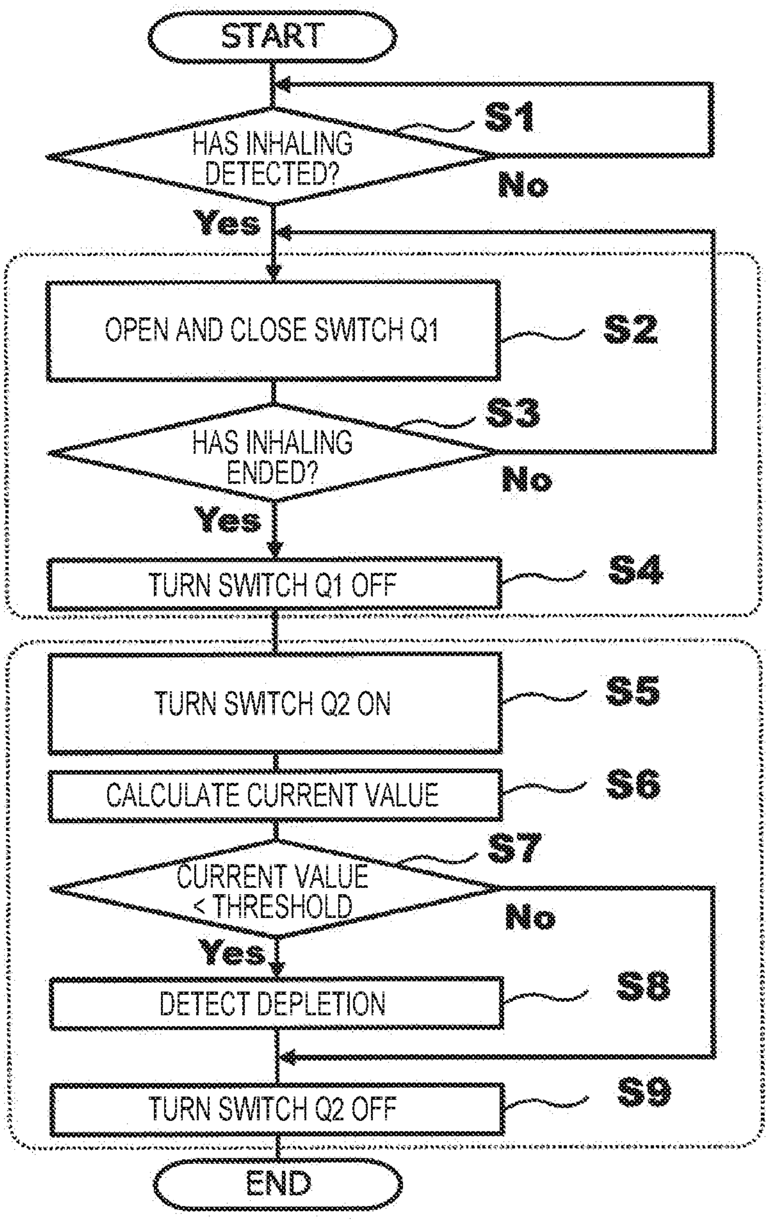
FIG. 6 is a processing flow diagram showing one example of remaining quantity estimation processing.
Figure 7:
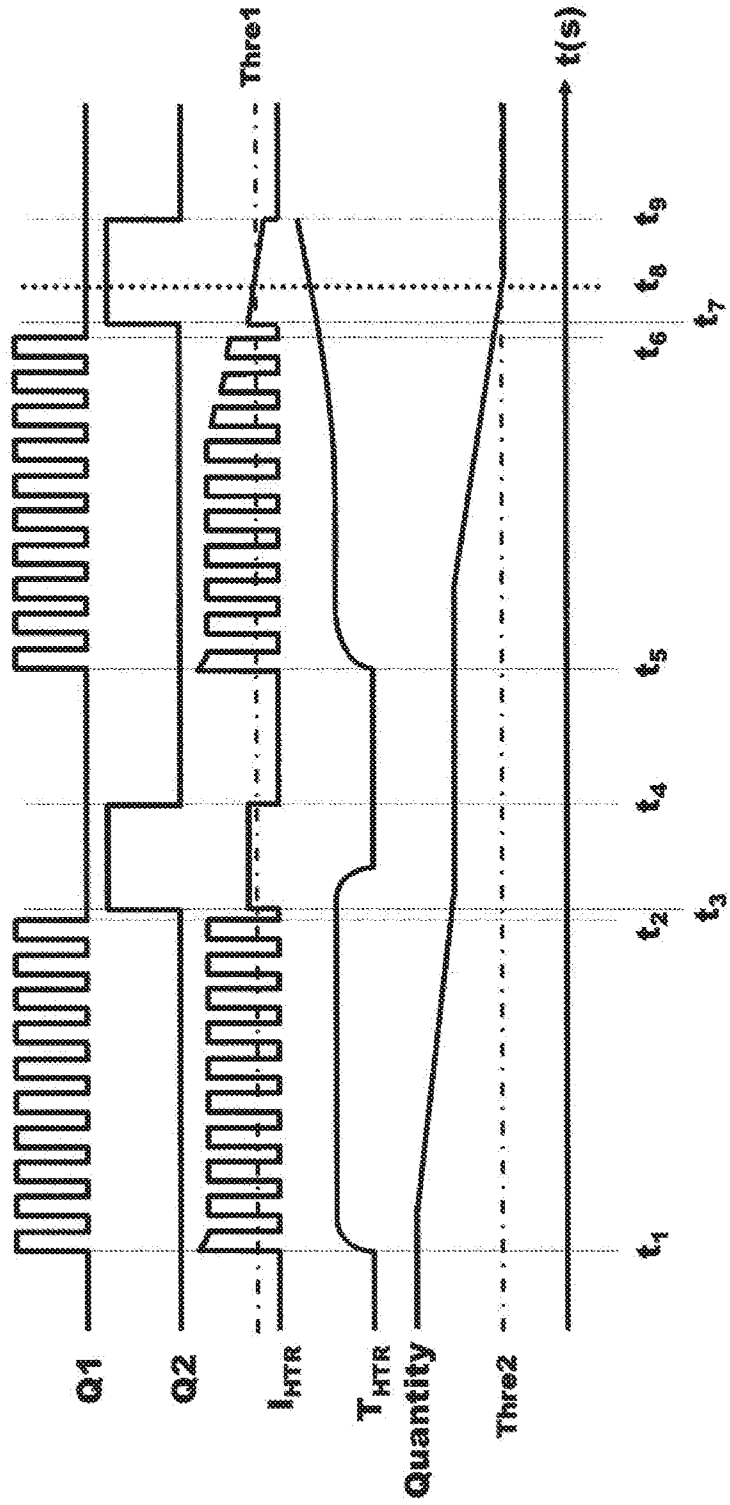
FIG. 7 is a timing chart showing one example of a state in which a user uses the aerosol generating apparatus.

FIG. 6 is a processing flow diagram showing one example of remaining quantity estimation processing. FIG. 7 is a timing chart showing one example of a state in which a user uses the aerosol generating apparatus. In FIG. 7, the direction of an arrow indicates passage of time t (s) and graphs respectively show opening and closing of the switches Q1 and Q2, the value $I_{HTR}$ of a current flowing through the load 33, the calculated temperature $T_{HTR}$ of the load 33, and a change in the remaining quantity of the aerosol source. Note that threshold values Thre1 and Thre2 are predetermined threshold values for detecting depletion of the aerosol source. The aerosol generating apparatus 1 estimates the remaining quantity when used by a user, and if a reduction in the aerosol source is detected, performs predetermined processing.

The control unit 22 of the aerosol generating apparatus 1 determines whether the user has performed an inhaling action, based on output of the inhalation sensor 23 (FIG. 6: step S1). In this step, if the control unit 22 detects generation of a negative pressure, a change in the flow rate, etc. based on output of the inhalation sensor 23, the control unit 22 determines that an inhaling action of the user is detected. If inhalation is not detected (step S1: No), the process performed in step S1 is repeated. Note that inhalation performed by the user may also be detected by comparing a negative pressure or a change in the flow rate with a threshold value other than 0.

On the other hand, if inhalation is detected (step S1: Yes), the control unit 22 performs Pulse Width Modulation (PWM) control on the switch Q1 (FIG. 6: step S2). Assume that inhalation is detected at time t1 in FIG. 7, for example. After time t1, the control unit 22 opens and closes the switch Q1 at a predetermined cycle. As the switch Q1 is opened and closed, a current flows through the load 33 and the temperature $T_{HTR}$ of the load 33 increases up to approximately the boiling point of the aerosol source. The aerosol source is heated with the temperature of the load 33 and evaporates, and the remaining quantity of the aerosol source decreases. Note that Pulse Frequency Modulation (PFM) control may also be used, instead of the PWM control, when controlling the switch Q1 in step S2.

The control unit 22 determines whether the inhaling action of the user has ended, based on output of the inhalation sensor 23 (FIG. 6: step S3). In this step, the control unit 22 determines that the user has ceased to inhale if generation of a negative pressure, a change in the flow rate, etc. is no longer detected based on output of the inhalation sensor 23. If inhalation has not ended (step S3: No), the control unit 22 repeats the process in step S2. Note that the end of the inhaling action of the user may also be detected by comparing a negative pressure or a change in the flow rate with a threshold value other than 0. Alternatively, when a predetermined period has elapsed from detection of the inhaling action of the user in step S1, the processing may be advanced to step S4 regardless of the determination made in step S3.

On the other hand, if inhalation has ended (step S3: Yes), the control unit 22 ceases the PWM control of the switch Q1 (FIG. 6: step S4). Assume that it is determined at time t2 in FIG. 7 that inhalation has ended, for example. After time t2, the switch Q1 enters an open state (OFF) and power supply to the load 33 ceases. The aerosol source is supplied from the storage portion 31 via the supply portion 32 to the load 33 and the temperature $T_{HTR}$ of the load 33 gradually decreases through dissipation. As a result of the temperature $T_{HTR}$ of the load 33 decreasing, evaporation of the aerosol source ceases and a reduction in the remaining quantity also ceases.

As described above, as a result of the switch Q1 being turned ON, a current flows through the aerosol generation path shown in FIG. 4 in steps S2 to S4 surrounded by a rounded rectangle indicated by a dotted line in FIG. 6.

Thereafter, the control unit 22 continuously closes the switch Q2 for a predetermined period (FIG. 6: step S5). As a result of the switch Q2 being turned ON, a current flows through the remaining quantity detection path shown in FIG. 4 in steps S5 to S9 surrounded by a rounded rectangle indicated by a dotted line in FIG. 6. At time t3 in FIG. 7, the switch Q2 is in a closed state (ON). In the remaining quantity detection path, the shunt resistor 341 is connected in series to the load 33. The remaining quantity detection path has a larger resistance value than the aerosol generation path as a result of the shunt resistor 341 being added, and the current value $I_{HTR}$ of a current flowing through the load 33 via the remaining quantity detection path is smaller than the current value $I_{HTR}$ of a current flowing through the load 33 via the aerosol generation path.

In the state in which the switch Q2 is closed, the control unit 22 acquires a measurement value from the remaining quantity sensor 34 and detects the current value of a current flowing through the shunt resistor 341 (FIG. 6: step S6). In this step, the current value $I_{shunt}$ at the shunt resistor 341 is calculated using the above-described expression (2) from a voltage between opposite ends of the shunt resistor 341 measured using the voltmeter 342, for example. Note that the current value $I_{shunt}$ at the shunt resistor 341 is equal to the current value $I_{HTR}$ of a current flowing through the load 33.

In the state in which the switch Q2 is closed, the control unit 22 determines whether or not the current value of a current flowing through the load 33 is smaller than a threshold value of the current determined in advance (FIG. 6: step S7). Namely, the control unit 22 determines whether the measurement value belongs to a prescribed range that includes a target value or a target range. Here, the threshold value (FIG. 7: Thre1) of the current corresponds to a threshold value (FIG. 7: Thre2) of the remaining quantity of the aerosol source determined in advance, with which it is to be determined that the aerosol source in the storage portion 31 is depleted. Namely, if the current value $I_{HTR}$ of a current flowing through the load 33 is smaller than the threshold value Thre1, it is possible to determine that the remaining quantity of the aerosol source is smaller than the threshold value Thre2.

If the current value $I_{HTR}$ becomes smaller than the threshold value Thre1 (step S7: Yes) within a predetermined period for which the switch Q2 is closed, the control unit 22 detects depletion of the aerosol source and performs predetermined processing (FIG. 6: step S8). If the voltage value measured in step S6 and the current value determined based on the voltage value are smaller than predetermined threshold values, the remaining quantity of the aerosol source is small, and accordingly control is performed in this step to further reduce the voltage value measured in step S6 and the current value determined based on the voltage value. For example, the control unit 22 may cease operations of the aerosol generating apparatus 1 by ceasing operations of the switch Q1 or Q2 or cutting off power supply to the load 33 using a power fuse (not shown), for example.

Note that, as is the case with the period from time t3 to time t4 in FIG. 7, if the remaining quantity of the aerosol source is sufficiently large, the current value $I_{HTR}$ is larger than the threshold value Thre1.

After step S8 or if the current value $I_{HTR}$ is at least the threshold value Thre1 (step S7: No) over the predetermined period for which the switch Q2 is closed, the control unit 22 opens the switch Q2 (FIG. 6: step S9). At time t4 in FIG. 7, the predetermined period has elapsed and the current value $I_{HTR}$ has been at least the threshold value Thre1, and therefore the switch Q2 is turned OFF. Note that the predetermined period (corresponding to the period from time t3 to time t4 in FIG. 7) for which the switch Q2 is closed is shorter than a period (corresponding to the period from time t1 to time t2 in FIG. 7) for which the switch Q1 is closed in steps S2 to S4. If it is determined in step S7 that the measurement value belongs to the prescribed range, when inhalation is detected thereafter (step S1: Yes), control is performed such that the current value (measurement value) to be calculated in step S6 approaches the target value or the target range by opening and closing the switch Q1 (step S2) while adjusting the duty ratio of the switching, for example. Here, control is performed such that the amount of change in the measurement value is larger in a case in which the feed circuit is controlled to reduce the amount of a current flowing to the load 33 (also referred to as a "second control mode" according to the present invention) when the measurement value does not belong to the prescribed range, than in a case in which the feed circuit is controlled to make the measurement value approach the target value or the target range (also referred to as a "first control mode" according to the present invention) when the measurement value belongs to the prescribed range.

Thus, the remaining quantity estimation processing ends. Thereafter, the processing returns to the process performed in step S1, and if an inhaling action of the user is detected, the processing shown in FIG. 6 is executed again.

At time t5 in FIG. 7, an inhaling action of the user is detected (FIG. 6: step S1: Yes), and PWM control of the switch Q1 is started. At time t6 in FIG. 7, it is determined that the inhaling action of the user has ended (FIG. 6: step S3: Yes), and the PWM control of the switch Q1 is ceased. At time t7 in FIG. 7, the switch Q2 is turned ON (FIG. 6: step S5), and the current value at the shunt resistor is calculated (FIG. 6: step S6). Thereafter, as shown in the period after time t7 in FIG. 7, the remaining quantity of the aerosol source becomes smaller than the threshold value Thre2 and the temperature $T_{HTR}$ of the load 33 increases. The current value $I_{HTR}$ of a current flowing through the load 33 decreases, and at time t8, the control unit 22 detects that the current value $I_{HTR}$ is smaller than the threshold value Thre1 (FIG. 6: step S7: Yes). In this case, it is found that the aerosol cannot be generated due to depletion of the aerosol source, and accordingly the control unit 22 does not open and close the switch Q1 even if an inhaling action of the user is detected at time t8 or later, for example. In the example shown in FIG. 7, the predetermined period thereafter elapses at time t9, and the switch Q2 is turned OFF (FIG. 6: step S9). Note that the control unit 22 may also turn the switch Q2 OFF at time t8 at which the current value $I_{HTR}$ becomes smaller than the threshold value Thre1.

As described above, in the present embodiment, the voltage conversion unit 211 that converts voltage is provided, and therefore it is possible to reduce errors that might be included in variables used for control when estimating the remaining quantity of the aerosol source or depletion thereof, and precision of control performed according to the remaining quantity of the aerosol source can be improved, for example.

<Determination Period>

In the remaining quantity determination processing performed in the above-described embodiment, the control unit 22 acquires the measurement value of the remaining quantity sensor 34 while keeping the switch Q2 ON for the predetermined period. Note that the period for which the switch Q2 is closed will be referred to as a "feeding sequence" for supplying power to the remaining quantity sensor 34 and the load 33. Here, a "determination period" for determining the remaining quantity of the aerosol source may also be used to determine the remaining quantity. The determination period is included in the feeding sequence on a time axis, for example, and the length of the determination period is changeable.

Figure 8:
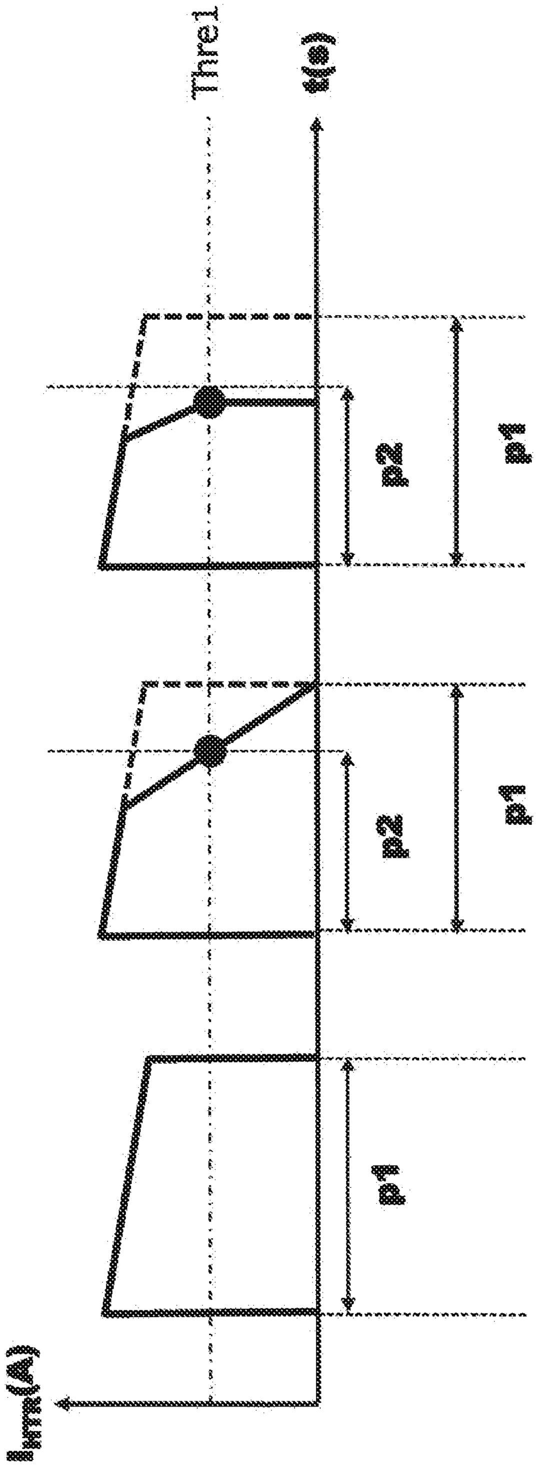
FIG. 8 is a diagram showing one example of a method for determining the length of a determination period.

FIG. 8 is a diagram showing one example of a method for determining the length of the determination period. In the graph shown in FIG. 8, the horizontal axis indicates passage of time t and the vertical axis indicates the current value $I_{HTR}$ of a current flowing through the load 33. In the example shown in FIG. 8, the current value $I_{HTR}$ of a current that flows when the switch Q1 is opened or closed is omitted for the sake of convenience, and only the current value $I_{HTR}$ of a current that flows through the load 33 in feeding sequences during which the switch Q2 is closed is shown.

Periods p1 shown in FIG. 8 are normal feeding sequences, and the current value $I_{HTR}$ shown on the left represents a schematic profile in a case in which a sufficient quantity of the aerosol source is remaining. Assume that the determination period is initially equal to the feeding sequence (p1). In the example shown on the left, the temperature $T_{HTR}$ of the load 33 increases as power is supplied, and the current value $I_{HTR}$ gradually decreases as a result of the resistance value $R_{HTR}$ of the load 33 increasing with the increase in the temperature $T_{HTR}$ of the load 33, but the current value $I_{HTR}$ does not become smaller than the threshold value Thre1. In such a case, the determination period is not changed.

The current value $I_{HTR}$ shown at the center represents a case in which the current value $I_{HTR}$ becomes smaller than the threshold value Thre1 within the determination period (p1). Here, a period p2 from the start of the feeding sequence to a time at which the current value $I_{HTR}$ becomes smaller than the threshold value Thre1 is set as the determination period to be included in the following feeding sequence. Namely, the determination period in the following feeding sequence is adjusted based on the period it takes for the current value $I_{HTR}$ to become smaller than the threshold value Thre1 in the preceding feeding sequence. In other words, the higher the possibility of depletion of the aerosol source is, the shorter the determination period is set. A configuration is also possible in which the length of the feeding sequence is used as a reference, and if the current value $I_{HTR}$ becomes smaller than the threshold value Thre1 within the feeding sequence (determination period), it is determined that the possibility of depletion of the aerosol source is at least a threshold value (also referred to as a "second threshold value" according to the present invention). In other words, the determination period is set to be shorter than the feeding sequence only when the possibility of depletion of the aerosol source is at least the threshold value.

The current value $I_{HTR}$ shown on the right represents a case in which the current value $I_{HTR}$ becomes smaller than the threshold value Thre1 within the determination period (p2). The quantity of the aerosol source held by the storage portion 31 continuously decreases while the aerosol generating apparatus 1 is used. Therefore, as the aerosol source is depleted, the period from the start of power supply to a time at which the current value $I_{HTR}$ becomes smaller than the threshold value Thre1 normally gets shorter and shorter. In the example shown in FIG. 8, it is determined that the aerosol source is depleted (i.e., abnormal) if more than a prescribed number of cases have consecutively occurred in which the current value $I_{HTR}$ becomes smaller than the threshold value Thre1 within the determination period, when the determination period is repeated while being changed as described above. Note that, if the aerosol source is depleted, power supply to the remaining quantity detection circuit may also be ceased as shown in FIG. 8.

Figure 9:
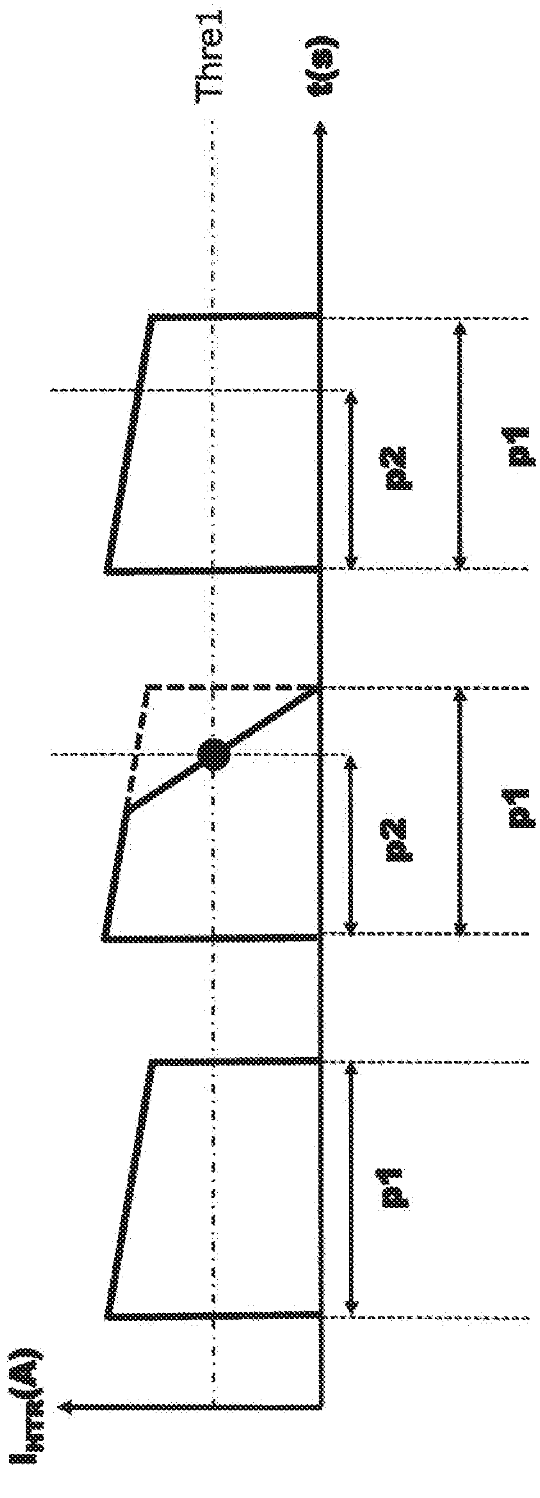
FIG. 9 is a diagram showing another example of changes in the current value of a current flowing through a load.

FIG. 9 is a diagram showing another example of changes in the current value of a current flowing through the load. The changes in the current value $I_{HTR}$ shown on the left and at the center of FIG. 9 are the same as those shown in FIG. 8. The current value $I_{HTR}$ shown on the right of FIG. 9 has the same profile as that in the case in which a sufficient quantity of the aerosol source is remaining, and does not become smaller than the threshold value Thre1 within the determination period (p2). Here, the aerosol generating apparatus 1 as shown in FIG. 3 is configured to supply the aerosol source from the storage portion 31 to the supply portion 32 using capillary action, and therefore, depending on the manner of inhalation performed by the user, it is difficult to control supply of the aerosol source using the control unit 22 etc. If the user inhales for a longer period than an envisaged period for a single puff or inhales at a shorter interval than an envisaged normal interval, the quantity of the aerosol source around the load 33 may temporarily become smaller than a normal quantity. In such a case, the current value $I_{HTR}$ may become smaller than the threshold value Thre1 within the determination period, as shown at the center of FIG. 9. If the user thereafter inhales in a different manner, the current value $I_{HTR}$ does not become smaller than the threshold value Thre1 within the determination period, as shown on the right of FIG. 9. Therefore, in the example shown in FIG. 9, the number of consecutive cases in which the current value $I_{HTR}$ becomes smaller than the threshold value Thre1 within the determination period is not larger than the prescribed number when the feeding period is repeated, and accordingly it is determined that the aerosol source stored in the storage portion 31 is not depleted.

If the above-described determination period is employed, precision of the determination as to whether or not the aerosol source is depleted can be further improved. Namely, the reference used in the determination operation can be adjusted by changing the determination period, and precision of the determination can be improved.

<Variation of Determination Processing>

Figure 10:
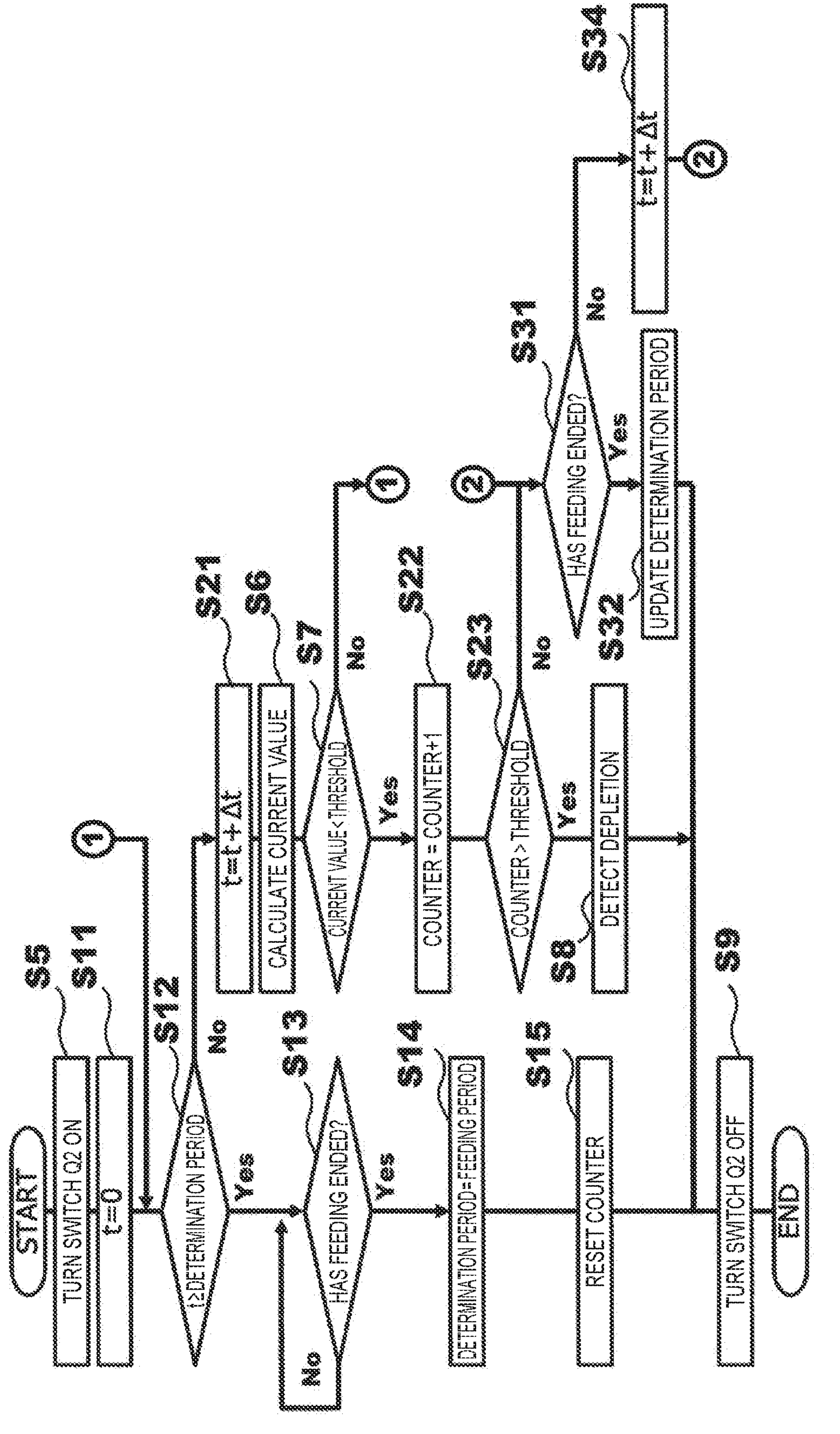
FIG. 10 is a processing flow diagram showing one example of processing for setting the determination period.

FIG. 10 is a processing flow diagram showing one example of processing for setting the determination period. In this variation, the control unit 22 executes determination processing shown in FIG. 10 instead of the processes performed in steps S5 to S9 in the remaining quantity estimation processing shown in FIG. 6.

First, the control unit 22 of the aerosol generating apparatus 1 turns the switch Q2 ON (FIG. 10: step S5). This step is the same as step S5 in FIG. 6.

Also, the control unit 22 activates a timer and starts to count an elapsed time t (FIG. 10: step S11).

Then, the control unit 22 determines whether the elapsed time t is at least the determination period (FIG. 10: step S12). If the elapsed time t is shorter than the determination period (step S12: No), the control unit 22 counts the elapsed time (FIG. 10: step S21). In this step, a difference Δt of a time elapsed from when the timer has been activated or the process in step S21 has been previously performed is added to t.

Also, the control unit 22 detects the current value $I_{HTR}$ of a current flowing through the load 33 (FIG. 10: step S6). The process performed in this step is the same as that performed in step S6 in FIG. 6.

Then, the control unit 22 determines whether the calculated current value $I_{HTR}$ is smaller than the predetermined threshold value Thre1 (FIG. 10: step S7). This step is similar to step S7 in FIG. 6. If the current value $I_{HTR}$ is equal to or larger than the threshold value Thre1 (step S7: No), the processing returns to the process performed in step S12.

In contrast, if the current value $I_{HTR}$ is smaller than the threshold value Thre1 (step S7: Yes), the control unit 22 adds 1 to a counter for counting the number of determination periods within which depletion is detected (FIG. 10: step S22).

Then, the control unit 22 determines whether the counter indicates a value that is larger than a prescribed value (threshold value) (step S23). If it is determined that the counter indicates a value larger than the prescribed value (step S23: Yes), the control unit 22 determines that depletion of the aerosol source is detected, and performs predetermined processing (FIG. 10: step S8). This step is the same as step S8 in FIG. 6.

In contrast, if it is determined that the counter indicates a value that is not larger than the prescribed value (step S23: No), the control unit 22 determines whether the feeding sequence has ended (FIG. 10: step S31). If the feeding sequence has not elapsed (step S31: No), the control unit 22 updates the elapsed time t and returns to the process performed in step S31.

In contrast, if it is determined that the feeding sequence has ended (step S31: Yes), the control unit 22 updates the determination period (FIG. 10: step S32). In this step, the elapsed time t at the point in time when it is determined in step S7 that the current value $I_{HTR}$ is smaller than the threshold value Thre1 is set as a new determination period. Namely, the determination period in the following feeding sequence is adjusted based on the period it takes for the measurement value to become smaller than the threshold value in the preceding feeding sequence. In other words, the length of the determination period in the following feeding sequence is adjusted based on the measurement value obtained in the preceding feeding sequence. This can also be said as adjusting the length of the determination period in a future feeding sequence based on the measurement value obtained in the current feeding sequence.

If it is determined in step S12 that the elapsed time t is at least the determination period (step S12: Yes), the control unit 22 determines whether the feeding sequence has ended (FIG. 10: step S13). If the feeding sequence has not ended (step S13: No), the control unit 22 continues to supply power until the feeding sequence ends. A state in which the determination period has elapsed and the feeding sequence has not elapsed is the state after the period p2 has elapsed and before the period p1 elapses in the period shown on the right of FIG. 9.

If it is determined that the feeding sequence has ended (step S13: Yes), the control unit 22 sets the length of the determination period to be equal to the length of the feeding sequence (FIG. 10: step S14).

Also, the control unit 22 resets the counter (FIG. 10: step S15). Namely, the counter for counting the number of consecutive determination periods within which depletion is detected is reset because the current value $I_{HTR}$ has not become smaller than the threshold value Thre1 within the determination period defined along with the feeding period. Note that a configuration is also possible in which the counter is not reset and, it is determined that there is an abnormality if the number of determination periods within which depletion is detected exceeds a predetermined threshold value.

After step S15, S8, or S32, the control unit 22 turns the switch Q2 OFF (FIG. 10: step S9). This step is the same as step S9 in FIG. 6.

Through the above-described processing, the changeable determination period shown in FIGS. 8 and 9 can be realized.

<Shunt Resistor>

The control unit 22 estimates the remaining quantity of the aerosol source by causing the remaining quantity detection path to function during a period for which the user does not inhale using the aerosol generating apparatus 1. However, it is not preferable that the aerosol is emitted from the mouthpiece during the period for which the user does not inhale. Namely, it is desirable that the quantity of the aerosol source evaporated by the load 33 while the switch Q2 is closed is as small as possible.

On the other hand, it is preferable that the control unit 22 can precisely detect a change in the remaining quantity of the aerosol source when the remaining quantity is small. Namely, the resolution increases as the measurement value of the remaining quantity sensor 34 largely changes according to the remaining quantity of the aerosol source, which is desirable. The following describes the resistance value of the shunt resistor based on these standpoints.

Figure 11:
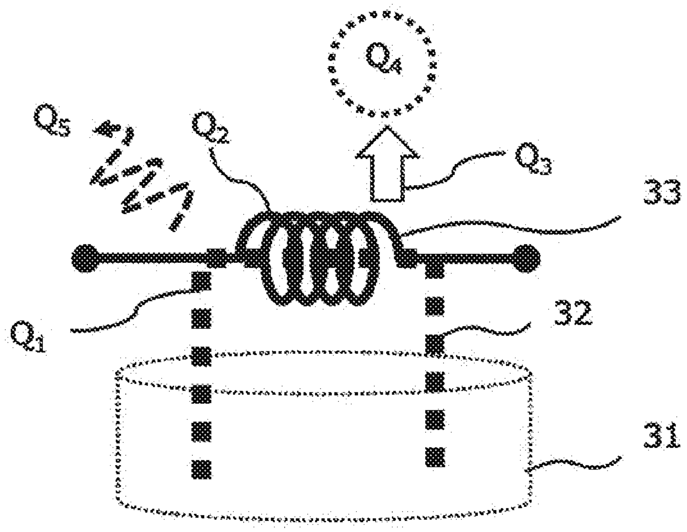
FIG. 11 is a diagram schematically showing energy consumed at the storage portion, a supply portion, and the load.

FIG. 11 is a diagram schematically showing energy consumed in the storage portion, the supply portion, and the load. $Q_1$ represents the quantity of heat generated by the wick of the supply portion 32, $Q_2$ represents the quantity of heat generated by the coil of the load 33, $Q_3$ represents the quantity of heat required for increasing the temperature of the aerosol source in a liquid state, $Q_4$ represents the quantity of heat required for changing the aerosol source from the liquid state to a gas state, and $Q_5$ represents heat generation in air through radiation etc. Consumed energy Q is the sum of $Q_1$ to $Q_5$.

The heat capacity C (J/K) of an object is a product of the mass m (g) of the object and the specific heat c (J/g·K) of the object. A heat quantity Q (J/K) required for changing the temperature of the object by T (K) can be expressed as m×C×T. Accordingly, if the temperature $T_{HTR}$ of the load 33 is lower than the boiling point Tb of the aerosol source, the consumed energy Q can be schematically expressed by the following expression (6). Note that $m_1$ represents the mass of the wick of the supply portion 32, $C_1$ represents the specific heat of the wick of the supply portion 32, $m_2$ represents the mass of the coil of the load 33, $C_2$ represents the specific heat of the coil of the load 33, $m_3$ represents the mass of the aerosol source in the liquid state, $C_3$ represents the specific heat of the aerosol source in the liquid state, and $T_0$ represents an initial value of the temperature of the load 33.

$$Q=(m_1C_1+m_2C_2+m_3C_3)(T_{HTR}-T_0) \tag{6}$$

If the temperature $T_{HTR}$ of the load 33 is equal to or higher than the boiling point Tb of the aerosol source, the consumed energy Q can be expressed by the following expression (7). Note that $m_4$ represents the mass of an evaporated portion of the liquid aerosol source and $H_4$ represents heat of evaporation of the liquid aerosol source.

$$Q=(m_1C_1+m_2C_2)(T_{HTR}-T_0)+m_3C_3(T_b-T_0)+m_4H_4 \tag{7}$$

Therefore, in order to prevent generation of the aerosol through evaporation, a threshold value $E_{thre}$ needs to satisfy a condition shown by the following expression (8).

$$E_{thre}<(m_1C_1+m_2C_2+m_3C_3)(T_b-T_0) \tag{8}$$

Figure 12:
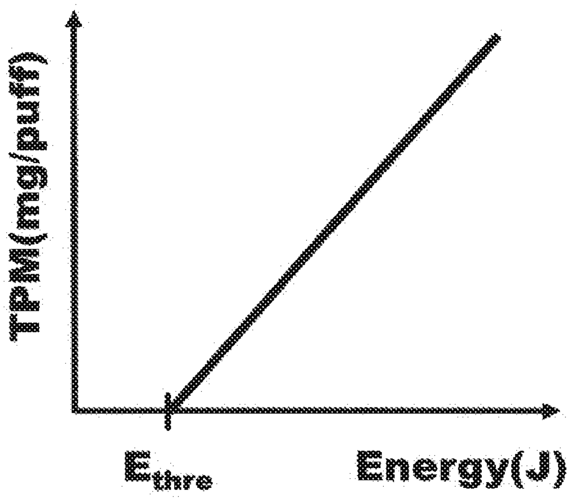
FIG. 12 is a graph schematically showing a relationship between energy consumed at the load and the quantity of a generated aerosol.

FIG. 12 is a graph schematically showing a relationship between energy (electric energy) consumed by the load 33 and the quantity of the generated aerosol. In FIG. 12, the horizontal axis indicates the energy and the vertical axis indicates TPM (Total Particle Matter: the quantity of substances forming the aerosol). As shown in FIG. 12, generation of the aerosol starts when the energy consumed by the load 33 exceeds the predetermined threshold value $E_{thre}$, and the quantity of the generated aerosol increases substantially in direct proportion to the consumed energy. Note that the vertical axis in FIG. 12 does not necessarily have to indicate the quantity of the aerosol generated by the load 33. For example, the vertical axis may also indicate the quantity of the aerosol generated through evaporation of the aerosol source. Alternatively, the vertical axis may also indicate the quantity of the aerosol emitted from the mouthpiece.

Here, energy $E_{HTR}$ consumed by the load 33 can be expressed by the following expression (9). Note that $W_{HTR}$ represents the power of the load 33 and $t_{Q2\_ON}$ represents a period (s) for which the switch Q2 is turned ON. Note that the switch Q2 needs to be turned ON for a certain period to measure the current value at the shunt resistor.

$$E_{HTR}=W_{HTR}\times t_{Q2\_ON} \tag{9}$$

The following expression (10) is obtained by transforming the expression (9) using a current value $I_{Q2}$ of a current flowing through the remaining quantity detection path, a resistance value $R_{HTR}$ ($T_{HTR}$) of the load 33 that varies according to the temperature $T_{HTR}$ of the load 33, and a measured voltage $V_{meas}$ of the shunt resistor.

$$E_{HTR}=W_{HTR}\times t_{Q2\_ON}=V_{HTR}\times I_{Q2}\times t_{Q2\_ON}= I_{Q2}^2\times R_{HTR}(T_{HTR})\times t_{Q2\_ON}=\left(\frac{V_{meas}}{R_{shunt}}\right)^2\times R_{HTR}(T_{HTR})\times t_{Q2\_ON} \tag{10}$$

Therefore, if the energy $E_{HTR}$ consumed by the load 33 is smaller than the threshold value $E_{thre}$ shown in FIG. 12 as expressed by the following expression (11), the aerosol is not generated.

$$E_{thre} > \left(\frac{V_{meas}}{R_{shunt}}\right)^2 \times R_{HTR}(T_{HTR}) \times t_{Q2\_ON} \tag{11}$$

This can be transformed to the following expression (12). Namely, if the resistance value $R_{shunt}$ of the shunt resistor satisfies the expression (12), the aerosol is not generated in the remaining quantity estimation processing, which is preferable.

$$R_{shunt} > V_{meas}\sqrt{\frac{R_{HTR}(T_{HTR}) \times t_{Q2\_ON}}{E_{thre}}} \tag{12}$$

Generally, it is preferable that the shunt resistor has a small resistance value, such as about several dozens of mΩ, to reduce effects on the circuit to which the shunt resistor is added. However, in the present embodiment, the lower limit of the resistance value of the shunt resistor is determined as described above from the standpoint of suppressing generation of the aerosol. The lower limit value is preferably about several Ω, for example, which is larger than the resistance value of the load 33. As described above, the resistance value of the shunt resistor is preferably set to satisfy a first condition that the quantity of the aerosol generated by the load in the feeding sequence during which power is supplied from the power source to the resistor is not larger than a predetermined threshold value.

Note that a configuration is also possible in which the resistance value of the shunt resistor is not increased, and an adjustment resistor is additionally provided in series to the shunt resistor to increase the total resistance value. In this case, a configuration is also possible in which a voltage between opposite ends of the added adjustment resistor is not measured.

Figure 13:
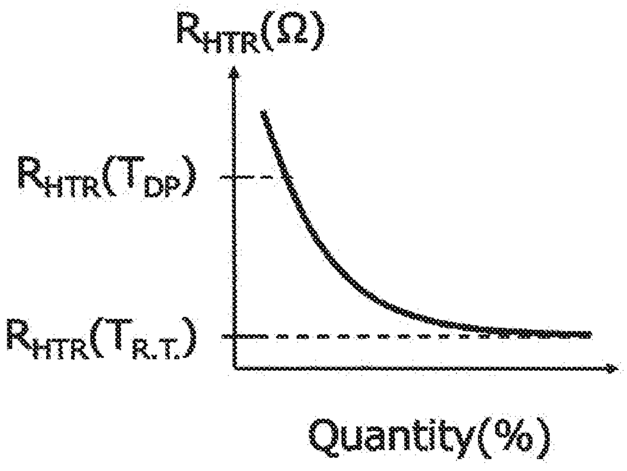
FIG. 13 is one example of a graph showing a relationship between the remaining quantity of an aerosol source and the resistance value of the load.

FIG. 13 is one example of a graph that shows a relationship between the remaining quantity of the aerosol source and the resistance value of the load 33. In the graph shown in FIG. 13, the horizontal axis indicates the remaining quantity of the aerosol source and the vertical axis indicates the resistance value of the load 33 determined according to the temperature of the load 33. $R_{HTR}$ ($T_{Depletion}$) represents a resistance value at a time when the aerosol source is depleted. $R_{HTR}$ ($T_{R.T.}$) represents a resistance value at the room temperature. Here, precision of estimation of the remaining quantity of the aerosol source can be improved by appropriately setting not only the voltage and the current, but also a measurement range of the resistance value or the temperature of the load 33, with respect to the resolution of the control unit 22 including the number of bits. On the other hand, as the difference between the resistance values $R_{HTR}$ ($T_{Depletion}$) and $R_{HTR}$ ($T_{R.T.}$) of the load 33 increases, the width of variation according to the remaining quantity of the aerosol source increases. In other words, precision of the estimated value of the remaining quantity calculated by the control unit 22 can be improved by increasing the width of variation of the resistance value of the load 33 that varies according to the temperature of the load 33, other than setting the resolution of the control unit 22 and the measurement range.

A current value $I_{Q2\_ON}$ ($T_{Depletion}$) that is detected based on an output value of the remaining quantity sensor 34 at a time when the aerosol source is depleted can be expressed by the following expression (13) using the resistance value $R_{HTR}$ ($T_{Depletion}$) of the load 33 at the time.

$$I_{Q2\_ON}(T_{Depletion}) = \frac{V_{out}}{R_{shunt} + R_{HTR}(T_{Depletion})} \tag{13}$$

Likewise, a current value $I_{Q2\_ON}$ ($T_{R.T.}$) that is detected based on an output value of the remaining quantity sensor 34 at a time when the load 33 is at the room temperature can be expressed by the following expression (14) using the resistance value $R_{HTR}$ ($T_{R.T.}$) of the load 33 at the time.

$$I_{Q2\_ON}(T_{R.T.}) = \frac{V_{out}}{R_{shunt} + R_{HTR}(T_{R.T.})} \tag{14}$$

Further, a difference $\Delta I_{Q2\_ON}$ obtained by subtracting the current value $I_{Q2\_ON}$ ($T_{Depletion}$) from the current value $I_{Q2\_ON}$ ($T_{R.T.}$) can be expressed by the following expression (15).

$$\Delta I_{Q2\_ON} = \frac{V_{out}}{R_{shunt} + R_{HTR}(T_{R.T.})} - \frac{V_{out}}{R_{shunt} + R_{HTR}(T_{Depletion})} = \frac{\{R_{HTR}(T_{Depletion}) - R_{HTR}(T_{R.T.})\} \times V_{out}}{\{R_{shunt} + R_{HTR}(T_{R.T.})\} \times \{R_{shunt} + R_{HTR}(T_{Depletion})\}} \tag{15}$$

It can be found from the expression (15) that, if $R_{shunt}$ is increased, the difference $\Delta I_{Q2\_ON}$ between the current value $I_{Q2\_ON}$ ($T_{R.T.}$) and the current value $I_{Q2\_ON}$ ($T_{Depletion}$) is reduced, and the remaining quantity of the aerosol source cannot be precisely estimated. Therefore, the resistance value $R_{shunt}$ of the shunt resistor is determined such that the difference $\Delta I_{Q2\_ON}$ is larger than a desired threshold value $\Delta I_{thre}$ as shown by the following expression (16).

$$\Delta I_{thre} < \frac{\{R_{HTR}(T_{Depletion}) - R_{HTR}(T_{R.T.})\} \times V_{out}}{\{R_{shunt} + R_{HTR}(T_{R.T.})\} \times \{R_{shunt} + R_{HTR}(T_{Depletion})\}} \tag{16}$$

By solving the expression (16) with respect to the resistance value $R_{shunt}$, a condition that is to be satisfied by the resistance value $R_{shunt}$ to sufficiently increase the resolution regarding the estimated value of the remaining quantity can be expressed by the following expression (17) using the desired threshold value $\Delta I_{thre}$. Therefore, the resistance value $R_{shunt}$ is set to satisfy the expression (17).

$$R_{shunt} < \frac{\sqrt{b^2 - 4c} - b}{2} \tag{17}$$

$$b = R_{HTR}(T_{Depletion}) + R_{HTR}(T_{R.T.})$$

$$c = R_{HTR}(T_{Depletion}) \times R_{HTR}(T_{R.T.}) + \frac{\{R_{HTR}(T_{R.T.}) - R_{HTR}(T_{Depletion})\} \times V_{out}}{\Delta I_{thre}}$$

In the present embodiment, the resistance value $R_{shunt}$ is set such that the difference $\Delta I_{Q2\_ON}$ between the current value $I_{Q2\_ON}$ ($T_{R.T.}$) of a current flowing through the load 33 at the room temperature and the current value $I_{Q2\_ON}$ ($T_{Depletion}$) of a current flowing through the load 33 when the aerosol source is depleted is large enough to be detected by the control unit 22. Alternatively, a configuration is also possible in which the resistance value $R_{shunt}$ is set such that a difference between the current value of a current flowing through the load 33 at approximately the boiling point of the aerosol source and the current value of a current flowing through the load 33 when the aerosol source is depleted is large enough to be detected by the control unit 22, for example. Generally, precision of estimation of the remaining quantity of the aerosol source is improved as the temperature difference corresponding to a current difference that can be detected by the control unit 22 is smaller.

The following more specifically describes effects that the resolution of the control unit 22 and settings of the remaining quantity detection circuit including the resistance value of the load 33 have on the precision of estimation of the remaining quantity of the aerosol source. If an n-bit microcontroller is used for the control unit 22 and $V_{REF}$ is applied as a reference voltage, the resolution of the control unit 22 can be expressed by the following expression (18).

$$\text{Resolution(V/bit)} = \frac{V_{REF}}{2^n} \tag{18}$$

A difference $\Delta V_{Q2\_ON}$ between a value that is detected by the voltmeter 342 when the load 33 is at the room temperature and a value that is detected by the voltmeter 342 when the aerosol source is depleted can be expressed by the following expression (19) based on the expression (15).

$$\Delta V_{Q2\_ON} = \frac{R_{shunt}}{R_{shunt}+R_{HTR}(T_{R.T.})}\times V_{out} - \frac{R_{shunt}}{R_{shunt}+R_{HTR}(T_{Depletion})}\times V_{out} = R_{shunt}\times V_{out}\times\left\{\frac{1}{R_{shunt}+R_{HTR}(T_{R.T})} - \frac{1}{R_{shunt}+R_{HTR}(T_{Depletion})}\right\} \tag{19}$$

Therefore, according to the expressions (18) and (19), the control unit 22 can detect a value expressed by the following expression (20) and integral multiples of this value as voltage differences, in the range from 0 to $\Delta V_{Q2\_ON}$.

$$\frac{\Delta V_{Q2\_ON}}{\text{Resolution}} = 2^n \times \frac{V_{out}}{V_{REF}} \times R_{shunt} \times \left\{\frac{1}{R_{shunt}+R_{HTR}(T_{R.T.})} - \frac{1}{R_{shunt}+R_{HTR}(T_{Depletion})}\right\} \tag{20}$$

Furthermore, according to the expression (20), the control unit 22 can detect a value expressed by the following expression (21) and integral multiples of this value as temperatures of the heater, in the range from the room temperature to the temperature of the load 33 at the time when the aerosol source is depleted.

$$\frac{(T_{Depletion}-T_{R.T.})\times\text{Resolution}}{\Delta V_{Q2\_ON}} = \frac{(T_{Depletion}-T_{R.T.})\times V_{REF}}{2^n\times V_{out}\times R_{shunt}} \times \left\{\frac{1}{R_{shunt}+R_{HTR}(T_{R.T.})} - \frac{1}{R_{shunt}+R_{HTR}(T_{Depletion})}\right\}^{-1} \tag{21}$$

Table 1 below shows one example of the resolution of the control unit 22 with respect to the temperature of the load 33 in cases in which variables in the expression (21) are changed.

TABLE 1

| Variable [unit] | Variation 1 | Variation 2 | Variation 3 | Variation 4 | Variation 5 |
|---|---|---|---|---|---|
| $T_{R.T.}$ [° C.] | 25 | 25 | 25 | 25 | 25 |
| $T_{Depletion}$ [° C.] | 400 | 400 | 400 | 400 | 400 |
| $V_{REF}$ [V] | 2 | 2 | 2 | 2 | 2 |
| n [bit] | 10 | 10 | 16 | 10 | 8 |
| $V_{out}$ [V] | 2.5 | 2.5 | 0.5 | 0.5 | 0.5 |
| $R_{shunt}$ [Ω] | 3 | 10 | 3 | 3 | 3 |
| $R_{HTR}$ ($T_{R.T.}$) [Ω] | 1 | 1 | 1 | 1 | 1 |
| $R_{HTR}$ ($T_{Depletion}$) [Ω] | 2 | 2 | 1.5 | 1.5 | 1.5 |
| Resolution [° C.] | 2.0 | 3.9 | 0.3 | 17.6 | 70.3 |

As apparent from Table 1, there is a tendency that the resolution of the control unit 22 with respect to the temperature of the load 33 largely changes when values of the variables are adjusted. In order to determine whether or not the aerosol source is depleted, the control unit 22 needs to be capable of distinguishing at least the room temperature, which is the temperature at a time when control is not performed or is started by the control unit 22, and the temperature at the time when the aerosol source is depleted. Namely, a measurement value of the remaining quantity sensor 34 obtained at the room temperature and a measurement value of the remaining quantity sensor 34 obtained at the temperature at the time when the aerosol source is depleted need to have a significant difference therebetween to be distinguishable for the control unit 22. In other words, the resolution of the control unit 22 with respect to the temperature of the load 33 needs to be not larger than a difference between the temperature at the time when the aerosol source is depleted and the room temperature.

As described above, if the remaining quantity of the aerosol source is sufficiently large, the temperature of the load 33 is kept near the boiling point of the aerosol source. In order to more accurately determine whether the aerosol source is depleted, it is preferable that the control unit 22 is capable of distinguishing the boiling point of the aerosol source and the temperature at the time when the aerosol source is depleted. Namely, it is preferable that a measurement value of the remaining quantity sensor 34 obtained at the boiling point of the aerosol source and a measurement value of the remaining quantity sensor 34 obtained at the temperature at the time when the aerosol source is depleted have a significant difference therebetween to be distinguishable for the control unit 22. In other words, it is preferable that the resolution of the control unit 22 with respect to the temperature of the load 33 is not larger than a difference between the temperature at the time when the aerosol source is depleted and the boiling point of the aerosol source.

Furthermore, if the remaining quantity sensor 34 is used not only for obtaining a measurement value to be used for determining whether or not the aerosol source is depleted, but also as a sensor for determining the temperature of the load 33, it is preferable that the control unit 22 is capable of distinguishing the room temperature, which is the temperature at a time when control is not performed or is started by the control unit 22, and the boiling point of the aerosol source. Namely, it is preferable that a measurement value of the remaining quantity sensor 34 obtained at the room temperature and a measurement value of the remaining quantity sensor 34 obtained at the boiling point of the aerosol source have a significant difference therebetween to be distinguishable for the control unit 22. In other words, it is preferable that the resolution of the control unit 22 with respect to the temperature of the load 33 is not larger than a difference between the boiling point of the aerosol source and the room temperature.

In order to use the remaining quantity sensor 34 for more precisely determining the temperature of the load 33, it is preferable that the resolution of the control unit 22 with respect to the temperature of the load 33 is not larger than 10° C. More preferably, the resolution is not larger than 5° C. Further preferably, the resolution is not larger than 1° C. In order to accurately distinguish a case in which the aerosol source is going to be depleted and a case in which the aerosol source has actually been depleted, it is preferable that the resolution of the control unit 22 with respect to the temperature of the load 33 is a divisor of a difference between the temperature at the time when the aerosol source is depleted and the room temperature.

Note that, as apparent from Table 1, the resolution of the control unit 22 with respect to the temperature of the load 33 can be easily improved by increasing the number of bits of the control unit 22, in other words, by improving the performance of the control unit 22. However, an increase in the performance of the control unit 22 leads to an increase in cost, weight, size, etc.

As described above, the resistance value of the shunt resistor can be determined to satisfy at least a first condition that the quantity of the aerosol generated by the load 33 is not larger than the predetermined threshold value or a second condition that a reduction in the remaining quantity of the aerosol source can be detected by the control unit 22 based on an output value of the remaining quantity sensor 34, and it is more preferable that the resistance value of the shunt resistor is determined to satisfy both the first condition and the second condition. A configuration is also possible in which the resistance value of the shunt resistor is closer to the largest value of values with which the second condition is satisfied than to the smallest value of values with which the first condition is satisfied. With this configuration, the resolution regarding detection of the remaining quantity can be improved as far as possible while suppressing generation of the aerosol during measurement. As a result, the remaining quantity of the aerosol source can be estimated not only precisely but also in a short period of time, and accordingly generation of the aerosol during measurement can be further suppressed.

It can be said that both the first condition and the second condition relate to responsiveness of a change in the current value of a current flowing through the load 33, which is the measurement value of the remaining quantity sensor 34, with respect to a change in the temperature of the load 33. A case in which responsiveness of a change in the current value of a current flowing through the load 33 with respect to a change in the temperature of the load 33 is strong is a case in which the load 33 is dominant in a combined resistance constituted by the shunt resistor 341 and the load 33 connected in series. Namely, the resistance value $R_{shunt}$ of the shunt resistor is small, and therefore the second condition can be easily satisfied, but the first condition is difficult to satisfy.

On the other hand, a case in which responsiveness of a change in the current value of a current flowing through the load 33 with respect to a change in the temperature of the load 33 is weak is a case in which the shunt resistor 341 is dominant in the combined resistance constituted by the shunt resistor 341 and the load 33 connected in series. Namely, the resistance value $R_{shunt}$ of the shunt resistor is large, and therefore the first condition can be easily satisfied, but the second condition is difficult to satisfy.

Namely, in order to satisfy the first condition, responsiveness of a change in the current value of a current flowing through the load 33 with respect to a change in the temperature of the load 33 needs to be not higher than a prescribed upper limit. On the other hand, in order to satisfy the second condition, responsiveness of a change in the current value of a current flowing through the load 33 with respect to a change in the temperature of the load 33 needs to be at least a prescribed lower limit. In order to satisfy both the first condition and the second condition, responsiveness of a change in the current value of a current flowing through the load 33 with respect to a change in the temperature of the load 33 needs to belong to a range that is defined by the prescribed upper limit and the prescribed lower limit.

<Circuit Variation 1>

Figure 14:
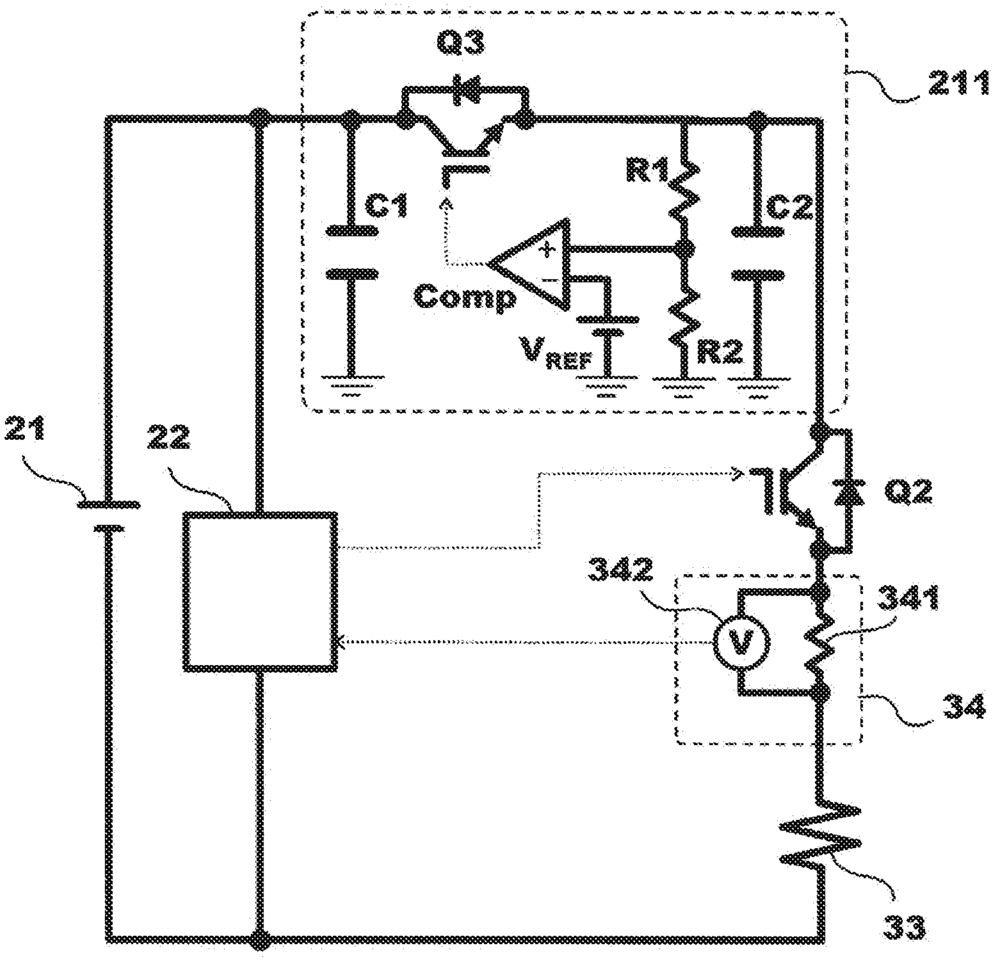
FIG. 14 is a diagram showing a variation of a circuit included in the aerosol generating apparatus.

FIG. 14 is a diagram showing a variation of the circuit included in the aerosol generating apparatus 1. In the example shown in FIG. 14, the remaining quantity detection path also serves as the aerosol generation path. Namely, the voltage conversion unit 211, the switch Q2, the remaining quantity sensor 34, and the load 33 are connected in series. Generation of an aerosol and estimation of the remaining quantity are performed using the single path. The remaining quantity can also be estimated with this configuration.

<Circuit Variation 2>

Figure 15:
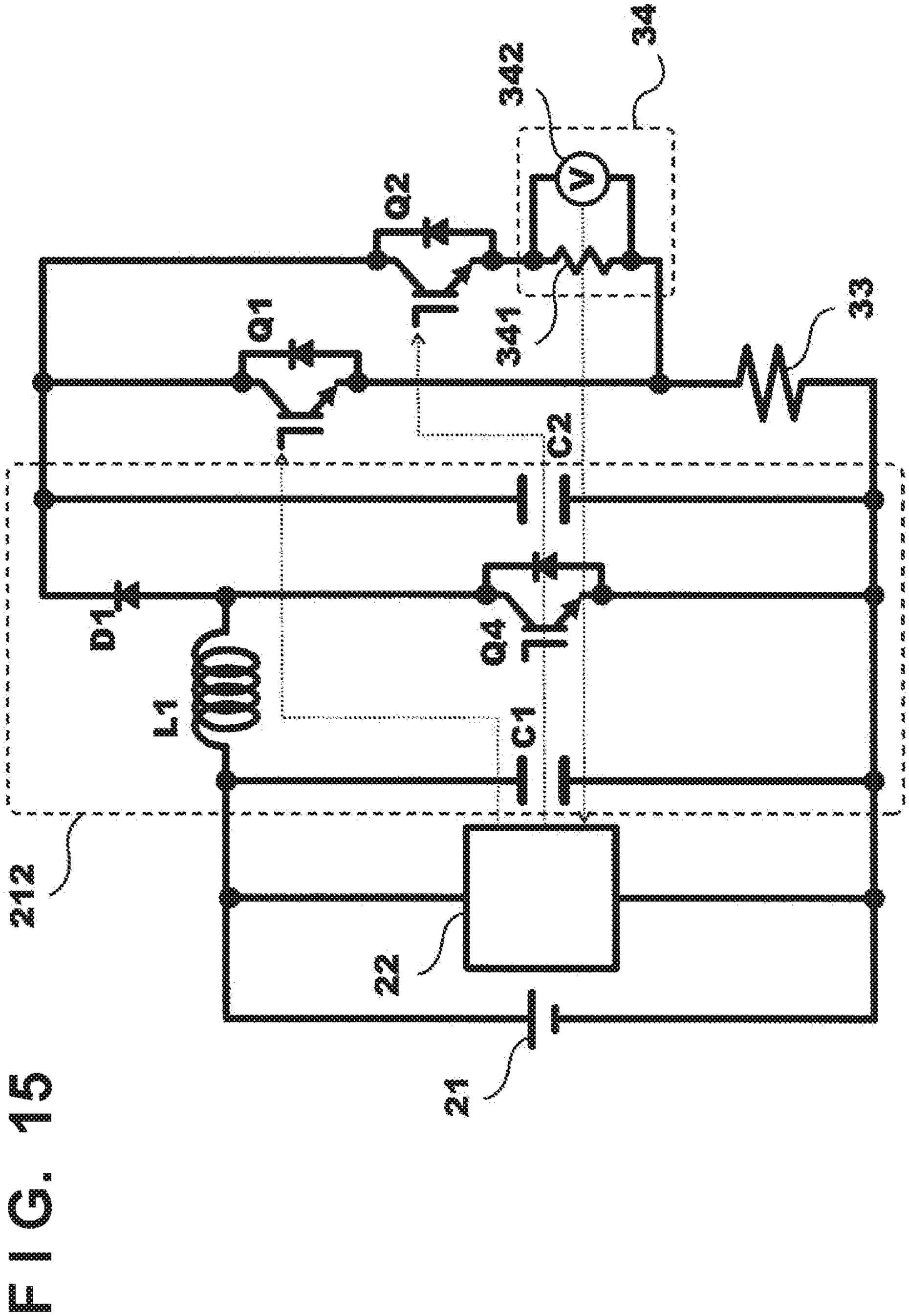
FIG. 15 is a diagram showing another variation of the circuit included in the aerosol generating apparatus.

FIG. 15 is a diagram showing another variation of the circuit included in the aerosol generating apparatus 1. The example shown in FIG. 15 includes a voltage conversion unit 212 that is a switching regulator, instead of a linear regulator. In one example, the voltage conversion unit 212 is a step-up converter and includes an inductor L1, a diode D1, a switch Q4, and capacitors C1 and C2 that function as smoothing capacitors. The voltage conversion unit 212 is provided upstream of a position at which a path extending from the power source 21 branches into the aerosol generation path and the remaining quantity detection path. Accordingly, mutually different voltages can be respectively output to the aerosol generation path and the remaining quantity detection path as a result of opening and closing of the switch Q4 of the voltage conversion unit 212 being controlled by the control unit 22. Note that, in a case in which a switching regulator is used instead of a linear regular as well, the switching regulator may be provided at the same position as that of the linear regulator shown in FIG. 14.

A configuration is also possible in which the voltage conversion unit 212 is controlled such that, when the aerosol generation path, which has less restrictions regarding voltage applied thereto when compared to the remaining quantity detection path to the entirety of which a constant voltage needs to be applied to detect the remaining quantity of the aerosol source, is caused to function, power loss is smaller than that occurs when the remaining quantity detection path is caused to function. With this configuration, wasting of the charge amount of the power source 21 can be suppressed. Also, the control unit 22 performs control such that a current that flows through the load 33 via the remaining quantity detection path is smaller than a current that flows through the load 33 via the aerosol generation path. Thus, generation of the aerosol at the load 33 can be suppressed while the remaining quantity of the aerosol source is estimated by causing the remaining quantity detection path to function.

A configuration is also possible in which, while the aerosol generation path is caused to function, the switching regulator is caused to operate in a "direct coupling mode" (also referred to as a "direct coupling state") in which switching of the low side switch Q4 is ceased and the switch Q4 is kept ON. Namely, the duty ratio of the switch Q4 may also be set to 100%. Loss that occurs when the switching regulator is switched includes transition loss and switching loss that accompany switching, in addition to conduction loss. However, if the switching regulator is caused to operate in the direct coupling mode, only conduction loss occurs at the switching regulator, and accordingly the use efficiency of the charge amount of the power source 21 is improved. A configuration is also possible in which the switching regulator is caused to operate in the direct coupling mode for a portion of a period for which the aerosol generation path is caused to function. In one example, if the charge amount of the power source 21 is sufficiently large and the output voltage of the power source 21 is high, the switching regulator is caused to operate in the direct coupling mode. On the other hand, if the charge amount of the power source 21 is small and the output voltage of the power source 21 is low, the switching regulator may be switched. With this configuration as well, the remaining quantity can be estimated, and loss can be reduced when compared to a case in which a linear regulator is used. Note that a step-down converter or a step-up/down converter may also be used instead of a step-up converter.

<Others>

The target to be heated by the aerosol generating apparatus may be a liquid flavor source that contains nicotine and other additive materials. In this case, a generated aerosol is inhaled by the user without passing through the additive component holding portion. In a case in which such a flavor source is used as well, the remaining quantity can be precisely estimated using the above-described aerosol generating apparatus.

The control unit 22 performs control such that the switches Q1 and Q2 are not turned ON at the same time. Namely, the control unit 22 performs control such that the aerosol generation path and the remaining quantity detection path do not function at the same time. A configuration is also possible in which a dead time for which both of the switches Q1 and Q2 are turned OFF is provided when switching opening and closing of the switches Q1 and Q2. This can prevent a situation in which a current flows through the two paths. On the other hand, it is preferable to make the dead time short to keep the temperature of the load 33 from decreasing during the dead time as far as possible.

The processing shown in FIG. 6 is described assuming that the remaining quantity estimation processing is performed one time for a single puff performed by a user. However, a configuration is also possible in which the remaining quantity estimation processing is performed one time for a plurality of puffs, rather than being performed for every puff. A configuration is also possible in which, after the aerosol source holding portion 3 is replaced, the remaining quantity estimation processing is started after a predetermined number of puffs, because a sufficient quantity of the aerosol source is remaining after the replacement. Namely, a configuration is also possible in which the frequency of power supply to the remaining quantity detection path is lower than the frequently of power supply to the aerosol generation path. With this configuration, the remaining quantity estimation processing is kept from being excessively performed and is executed only at appropriate timings, and accordingly the use efficiency of the charge amount of the power source 21 is improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An aerosol generating apparatus comprising:

a power source;

a load configured to have an electric resistance value that varies according to a temperature and atomize an aerosol source or heat a flavor source when supplied with power from the power source;

a feed circuit that is electrically connected to the power source and the load and includes a voltage converter configured to convert an output voltage of the power source and outputting the converted output voltage to the load; and processing circuitry configured to acquire a measurement value corresponding to a current value of a current flowing through the load and control power supply to the load based on the measurement value, wherein the feed circuit includes:

a sensor that is arranged at a position in series to the load and capable of outputting, as the measurement value, a current value of a current passing therethrough or a voltage value of a voltage applied thereto, a first power supply path that connects the power source to the load not via the sensor and a second power supply path that connects the power source to the load via the sensor, and a first node that is connected to the power source and from which the feed circuit branches into the first power supply path and the second power supply path and a second node that is connected to the load and at which the first power supply path and the second power supply path merge with each other, wherein the voltage converter includes a switching regulator, the switching regulator being provided between the power source and the first node in the feed circuit, wherein the processing circuitry controls the first power supply path and the second power supply path to not function at the same time and acquires the measurement value from the sensor included in the second power supply path, in a case that the first power supply path is caused to function, the processing circuitry controls the switching regulator in a direct coupling state, in a case that the measurement value belongs to a prescribed range that includes a target value or a target range, the processing circuitry controls the feed circuit such that the measurement value approaches the target value or the target range, and in a case that the measurement value does not belong to the prescribed range, the processing circuitry controls the feed circuit such that the measurement value becomes smaller than the target value or values included in the target range.

2. The aerosol generating apparatus of claim 1, wherein the second power supply path is configured such that a current that flows through the second power supply path is smaller than a current that flows through the first power supply path.

3. The aerosol generating apparatus of claim 1, wherein the voltage converter is configured to convert the output voltage of the power source such that a current that flows through the second power supply path is smaller than a current that flows through the first power supply path.

4. The aerosol generating apparatus of claim 1, wherein the processing circuitry is configured to control the first power supply path and the second power supply path such that a period for which power is supplied to the second power supply path is shorter than a period for which power is supplied to the first power supply path.

5. The aerosol generating apparatus of claim 1, wherein the processing circuitry is configured to control the first power supply path and the second power supply path such that the frequency of power supply to the second power supply path is lower than the frequency of power supply to the first power supply path.

6. The aerosol generating apparatus of claim 1, wherein the processing circuitry is configured to control the second power supply path such that an amount of an aerosol generated by the load while the second power supply path is caused to function is smaller than an amount of the aerosol generated by the load while the first power supply path is caused to function.

7. The aerosol generating apparatus of claim 1, further comprising:

a mouthpiece end that is provided at an end portion of the aerosol generating apparatus to emit an aerosol, wherein the processing circuitry is configured to control the second power supply path such that the aerosol is not emitted from the mouthpiece end while the second power supply path is caused to function.

8. The aerosol generating apparatus of claim 1, wherein the processing circuitry is configured to control the second power supply path such that the load does not generate an aerosol while the second power supply path is caused to function.

9. The aerosol generating apparatus of claim 1, wherein the voltage converter includes a linear regulator, which is provided between the first node and the sensor on the second power supply path.

10. The aerosol generating apparatus of claim 1, wherein the processing circuitry is configured to control the switching regulator such that power loss that occurs at the switching regulator when the first power supply path is caused to function is smaller than power loss that occurs at the switching regulator when the second power supply path is caused to function.

11. The aerosol generating apparatus of claim 1, wherein in a case that the measurement value does not belong to the prescribed range, the processing circuitry is configured to control the feed circuit such that a current does not flow through the load.

* * * * *